United States Patent
Murase et al.

(10) Patent No.: US 10,966,911 B2
(45) Date of Patent: Apr. 6, 2021

(54) MELANIN DECOMPOSITION INHIBITOR

(71) Applicant: KAO CORPORATION, Tokyo (JP)

(72) Inventors: Daiki Murase, Tochigi (JP); Akira Hachiya, Cincinnati, OH (US); Naoki Oya, Kamakura (JP); Kei Takano, Tokyo (JP); Akiko Kawasaki, Utsunomiya (JP); Keigo Kawabata, Odawara (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 16/075,828

(22) PCT Filed: Feb. 10, 2017

(86) PCT No.: PCT/JP2017/004987
§ 371 (c)(1),
(2) Date: Aug. 6, 2018

(87) PCT Pub. No.: WO2017/138652
PCT Pub. Date: Aug. 17, 2017

(65) Prior Publication Data
US 2019/0053994 A1    Feb. 21, 2019

Related U.S. Application Data

(60) Provisional application No. 62/294,667, filed on Feb. 12, 2016.

(30) Foreign Application Priority Data

Nov. 7, 2016  (JP) .............................. JP2016-217082

(51) Int. Cl.
| | |
|---|---|
| *A61Q 5/00* | (2006.01) |
| *A61Q 19/00* | (2006.01) |
| *A61K 31/155* | (2006.01) |
| *A61K 8/43* | (2006.01) |
| *A61K 8/49* | (2006.01) |
| *A61K 31/4741* | (2006.01) |
| *A61K 36/29* | (2006.01) |
| *A61K 36/71* | (2006.01) |
| *A61K 36/756* | (2006.01) |
| *A61K 8/97* | (2017.01) |
| *A61K 36/718* | (2006.01) |
| *A61K 8/41* | (2006.01) |
| *A61K 8/9789* | (2017.01) |

(52) U.S. Cl.
CPC ............. *A61K 8/4926* (2013.01); *A61K 8/41* (2013.01); *A61K 8/43* (2013.01); *A61K 8/49* (2013.01); *A61K 8/97* (2013.01); *A61K 8/9789* (2017.08); *A61K 31/155* (2013.01); *A61K 31/4741* (2013.01); *A61K 36/29* (2013.01); *A61K 36/71* (2013.01); *A61K 36/718* (2013.01); *A61K 36/756* (2013.01); *A61Q 5/00* (2013.01); *A61Q 19/00* (2013.01); *Y02A 50/30* (2018.01)

(58) Field of Classification Search
CPC ....... A61K 31/155; A61Q 5/002; A61Q 19/00
See application file for complete search history.

(56) References Cited

U.S. PATENT DOCUMENTS

| | | | |
|---|---|---|---|
| 6,413,993 B1 * | 7/2002 | Chulay ............... | A61K 31/155 514/350 |
| 2012/0114676 A1 * | 5/2012 | Thompson ............. | A61P 35/02 424/184.1 |
| 2013/0324587 A1 * | 12/2013 | Murase ............. | G01N 33/5044 514/44 A |

FOREIGN PATENT DOCUMENTS

| | | | | |
|---|---|---|---|---|
| CN | 102088956 A | 6/2011 | | |
| CN | 102266499 A | 12/2011 | | |
| CN | 104254615 A | 12/2014 | | |
| EP | 2843055 A4 | 3/2015 | | |
| FR | 2901133 A1 * | 11/2007 | .............. | A61K 8/19 |
| FR | 2901133 B1 * | 4/2013 | .......... | A61K 31/155 |
| JP | 05078222 A * | 3/1993 | | |
| JP | H05-078222 A | 3/1993 | | |
| JP | 2001-288052 A | 10/2001 | | |
| JP | 2001-342112 A | 12/2001 | | |
| JP | 2003-171240 A | 6/2003 | | |
| JP | 2011-074022 A | 4/2011 | | |
| WO | WO-2009137100 A2 * | 11/2009 | .............. | A61P 17/00 |
| WO | WO 2013/162012 A | 10/2013 | | |

OTHER PUBLICATIONS

Reactions vol. 1499, p. 8 published May 2014. (Year: 2014).*
Browne et al., British Medical Journal vol. 5225 pp. 550-551. Published 1961. (Year: 1961).*
Van Neste et al., Micron vol. 35, pp. 193-200. Published 2004 (Year: 2004).*
Reagan-Shaw et al., (FASEBJ vol. 22 pp. 659-661, Published 2007) (Year: 2007).*
International Search Report (ISR) for PCT/JP2017/004987; I.A. fd Feb. 10, 2017, dated May 9, 2017 from the Japan Patent Office, Tokyo, Japan.
International Preliminary Report on Patentability (IPRP), Chapter I of the Patent Cooperation Treaty, including the Written Opinion for PCT/JP2017/004987; I.A. fd Feb. 10, 2017, dated Aug. 14, 2018, by the International Bureau of WIPO, Geneva, Switzerland.

(Continued)

*Primary Examiner* — Theodore R. Howell
*Assistant Examiner* — George W Kosturko
(74) *Attorney, Agent, or Firm* — Sterne, Kessler, Goldstein & Fox P.L.L.C.

(57) ABSTRACT

To provide an inhibitor of melanin decomposition, which inhibits decomposition of melanin in keratinocytes to accelerate accumulation of melanin in skin and hair.

An inhibitor of melanin decomposition in keratinocytes, comprising at least one selected from the group consisting of a plant extract containing berberine or a salt thereof, berberine or a salt thereof, proguanil or a salt thereof and phenformin or a salt thereof, as an active ingredient.

12 Claims, 15 Drawing Sheets

(56) References Cited

OTHER PUBLICATIONS

Egan,, DF et al., "Phosphorylation of ULK1 (hATG1) by AMP-activated protein kinase connects energy sensing to mitophagy," Science. Jan. 28, 2011;331(6016):456-61. doi: 10.1126/science.1196371. Epub Dec. 23, 2010, Am. Assoc. Adv. Sci, Washington, DC.

Jeong, HW et al., "Berberine suppresses proinflammatory responses through AMPK activation in macrophages," Am J Physiol Endocrinol Metab. Apr. 2009;296(4):E955-64. doi: 10.1152/ajpendo.90599.2008. Epub Feb. 10, 2009, American Physiological Society, Bethesda, MD.

Yoon, J et al., "Complementary and alternative medicine for vitiligo," Chapter 10 in Vitiligo—Management and Therapy, Dr. Kelly KyungHwa Park, ed., ISBN: 978-953-307-731-4, published Dec. 14, 2011, IntechOpen, publisher.

The extended European search report, including the supplementary European search report and the European search opinion, for EP Appl. No. 17750373.7, dated Jun. 7, 2019, European Patent Office, Munich, Germany.

Abstract of Lee, Jong-Gu et al., "Isolation of melanin biosynthesis inhibitory compounds from the Phellodendri Cortex," Korean Journal of Pharmacognosy 38(4):387-393 (Dec. 30, 2007).

Song, Young Chan et al., "Berberine regulates melanin synthesis by activating PI3K/AKT, ERK and GSK3β in B16F10 melanoma cells," Int J Mol Med. Apr. 2015;35(4):1011-6. doi: 10.3892/ijmm.2015.2113. Epub Feb. 26, 2015.

Choi, Hye-In et al., "Melanosome uptake is associated with the proliferation and differentiation of keratinocytes," Arch Dermatol Res. Jan. 2014;306(1):59-66. doi: 10.1007/s00403-013-1422-x. Epub Oct. 31, 2013.

\* cited by examiner

[Figure 1]
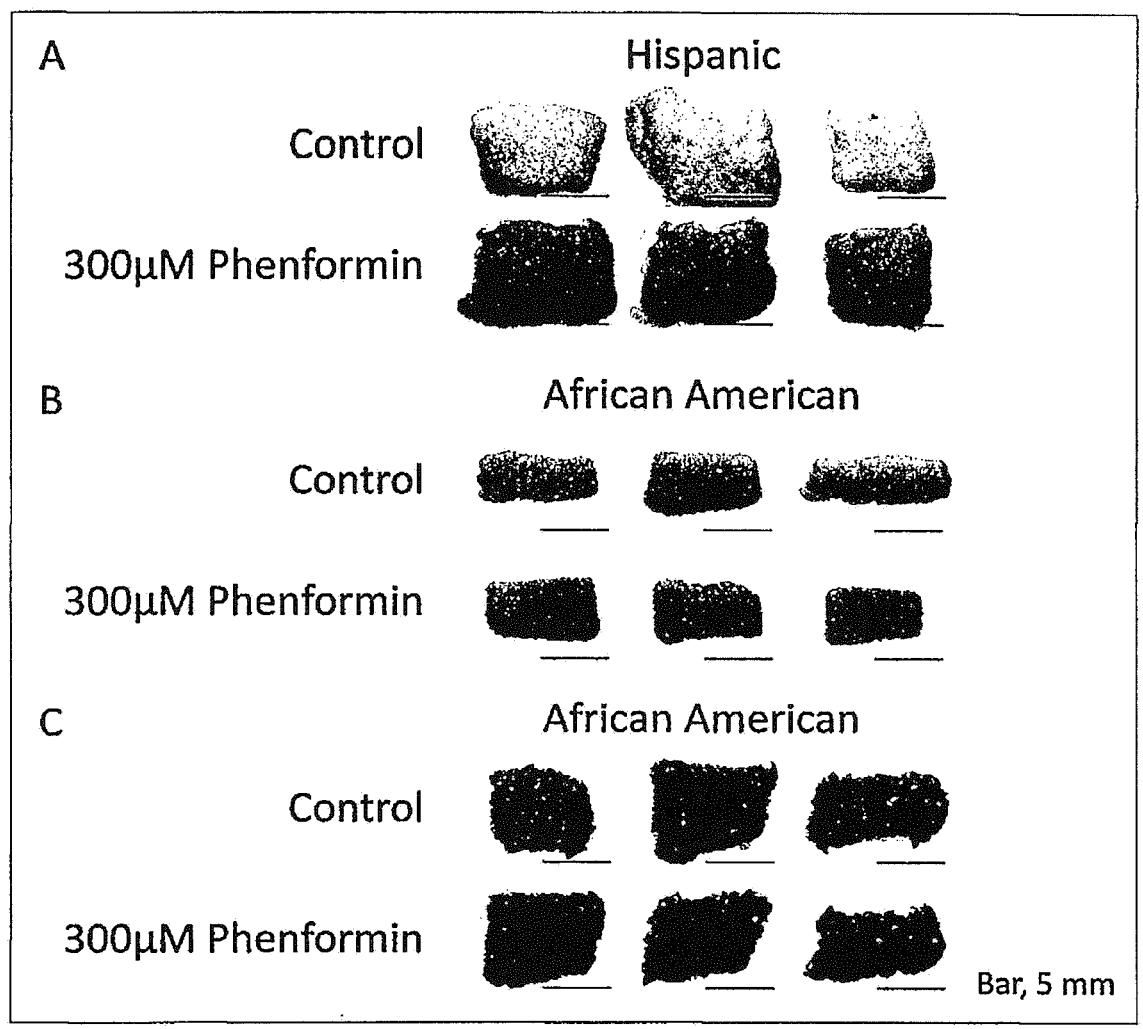

[Figure 2]
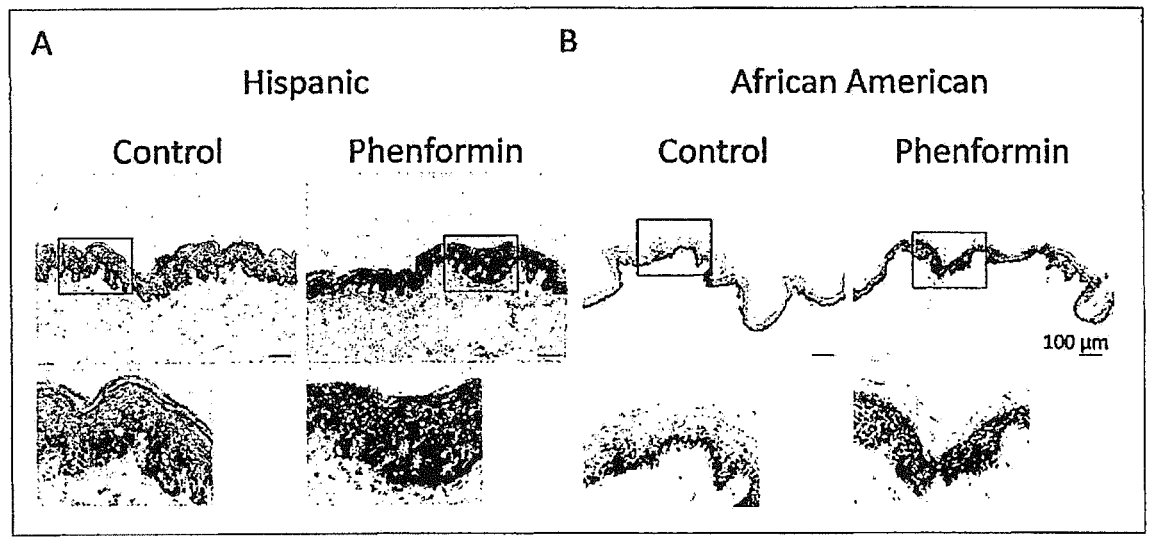
[Figure 3]
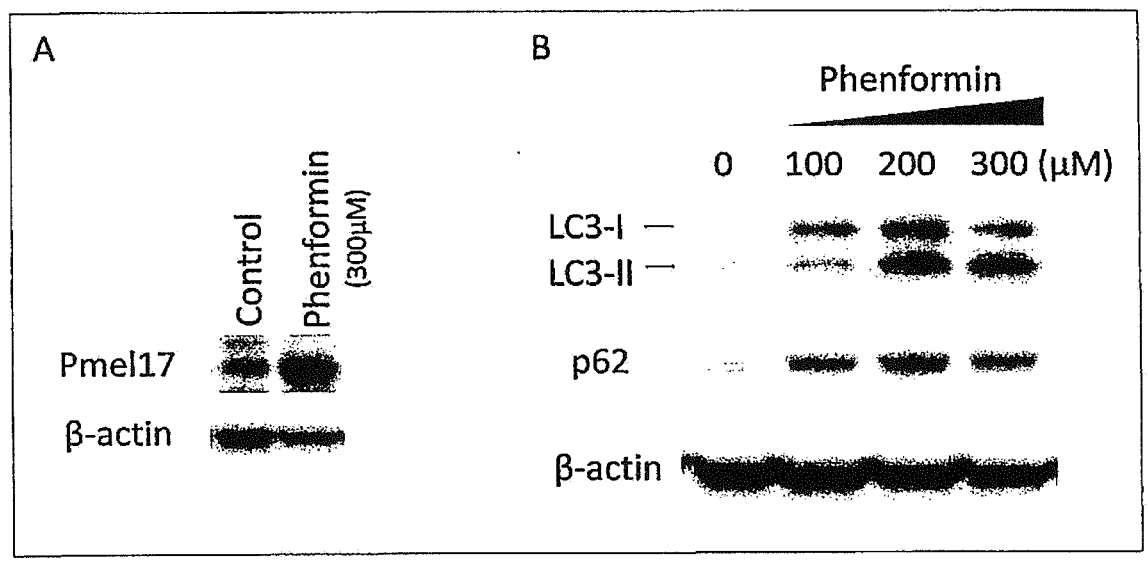

[Figure 4]
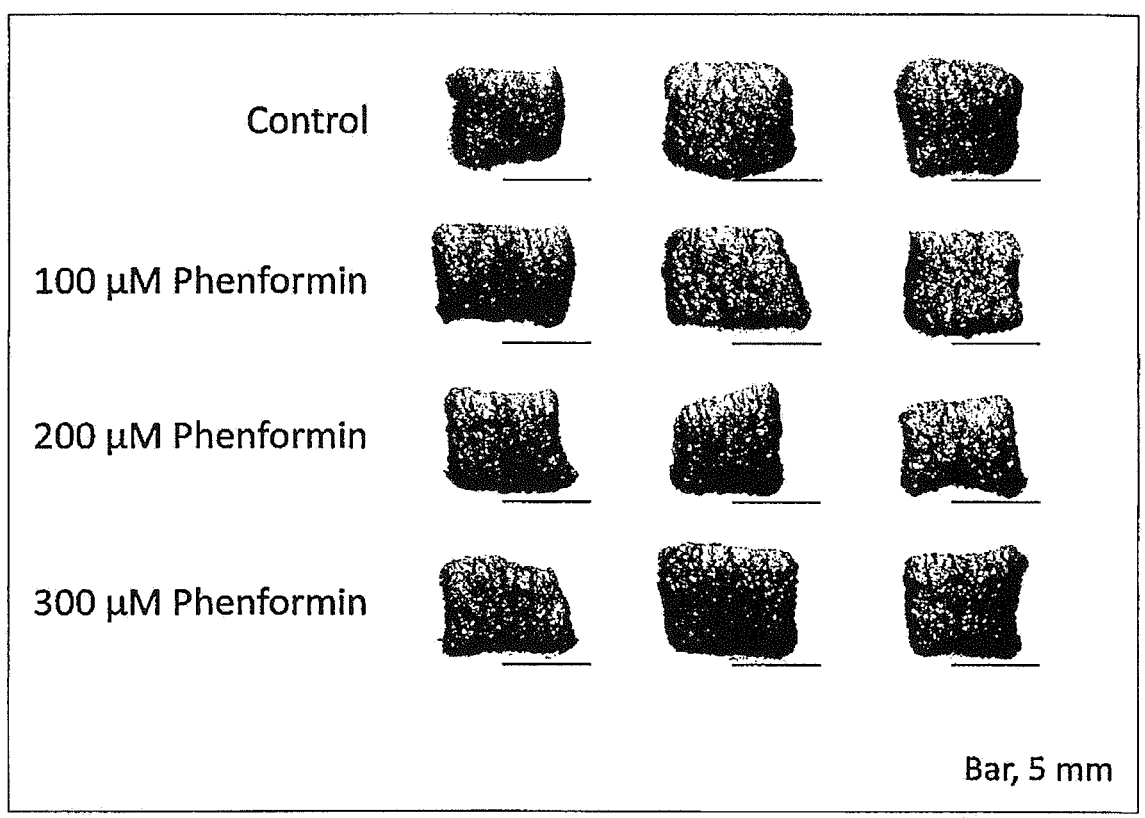

[Figure 5]
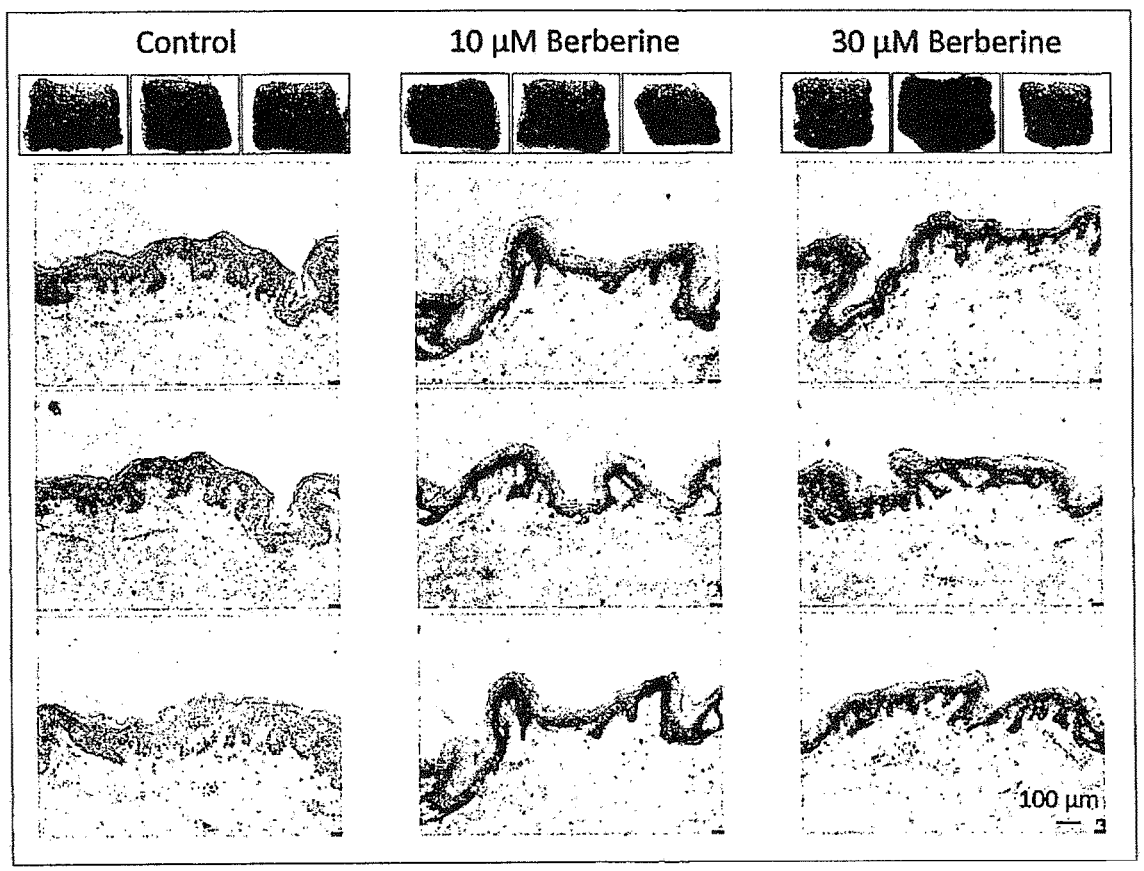

[Figure 6]
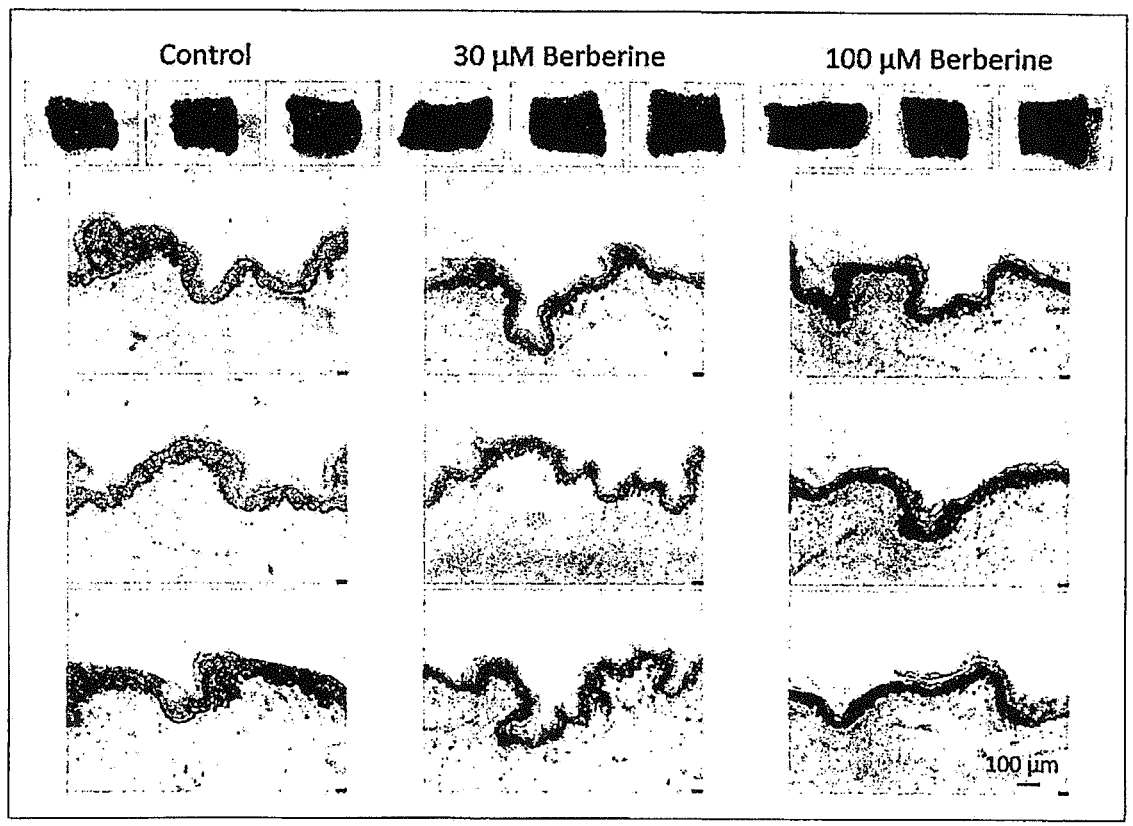

[Figure 7]
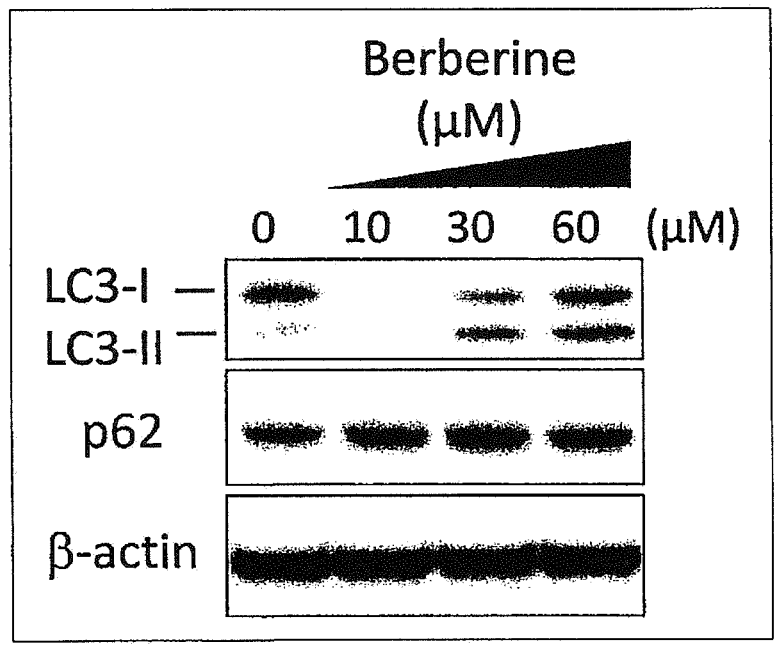
[Figure 8]
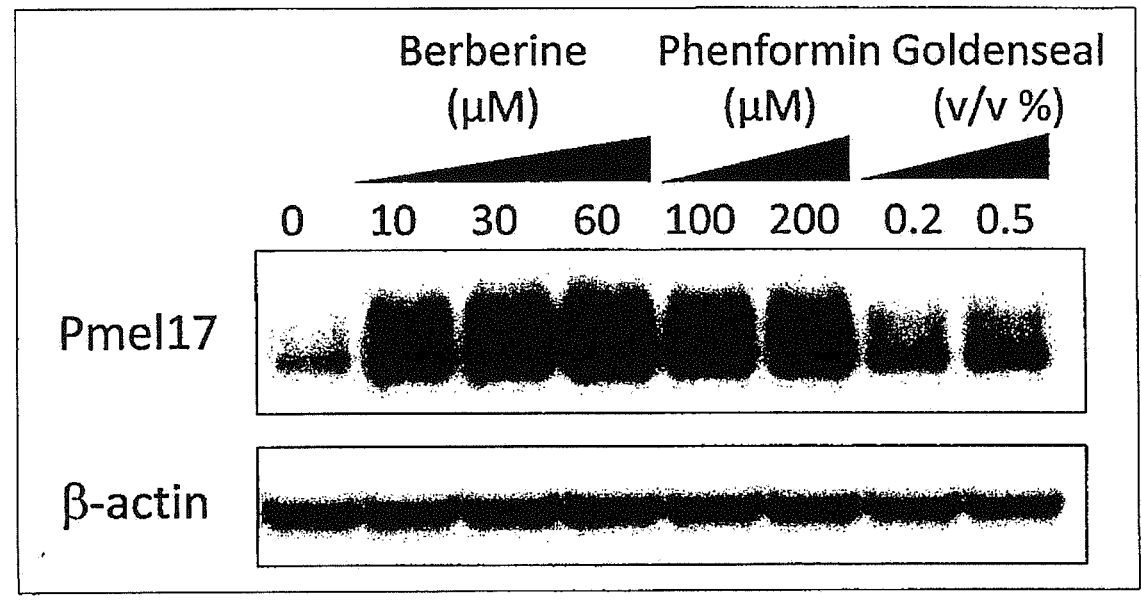

[Figure 9]
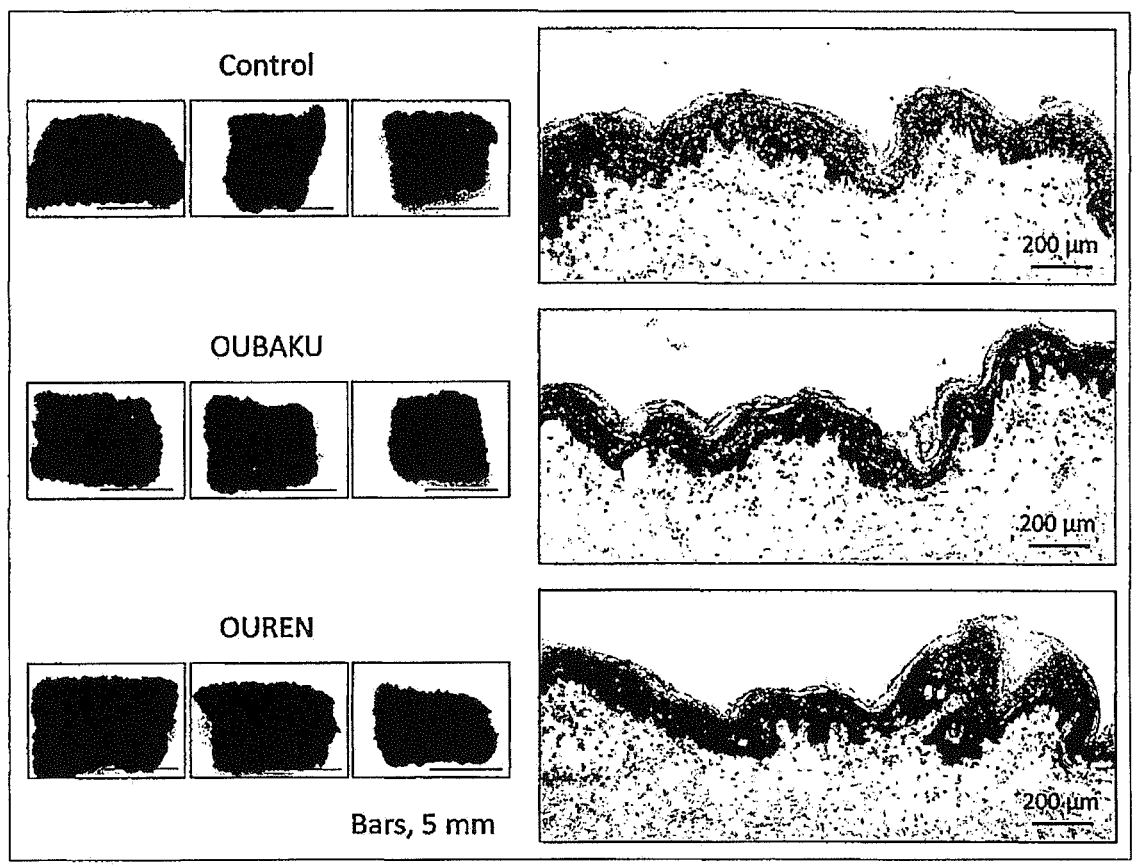

[Figure 10]
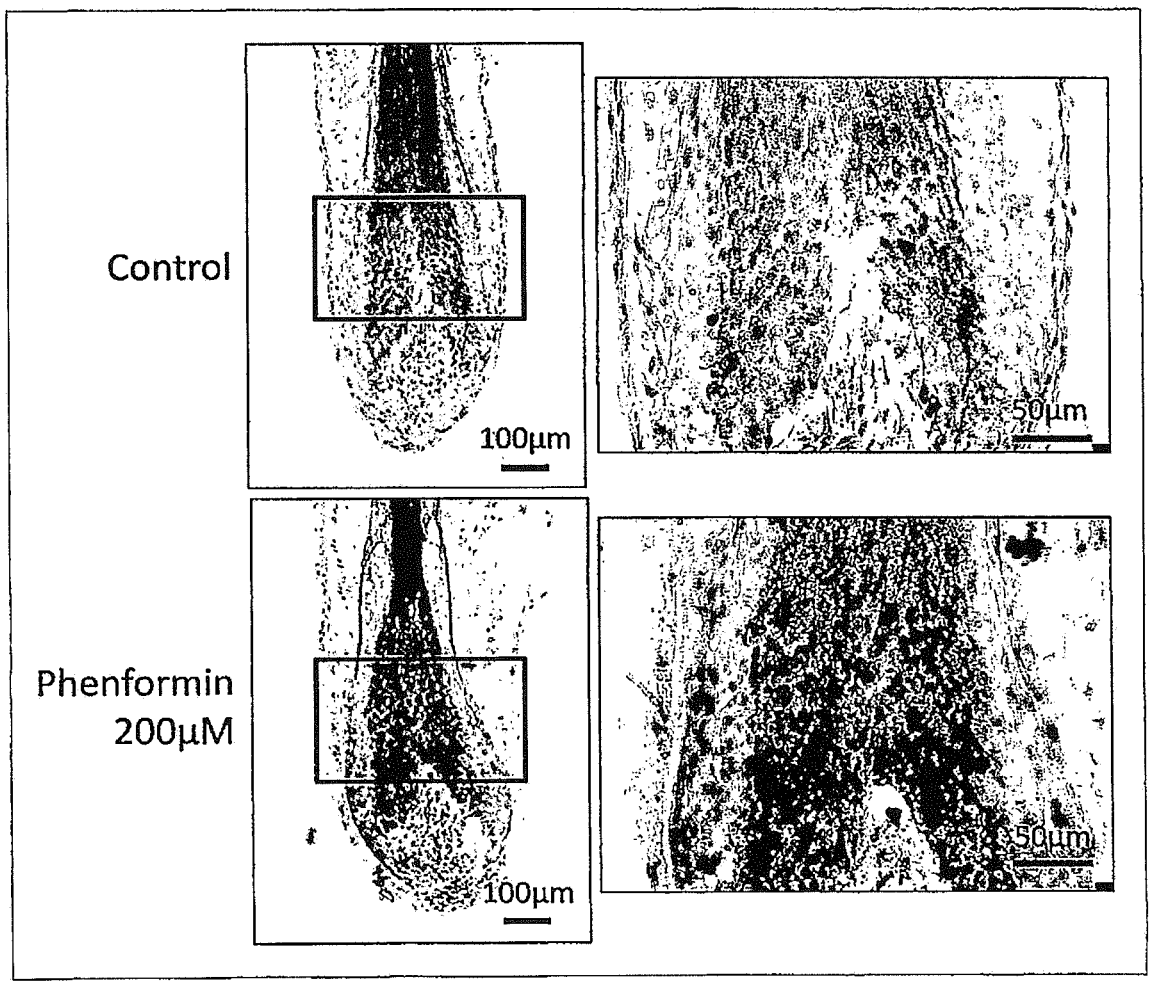

[Figure 11]
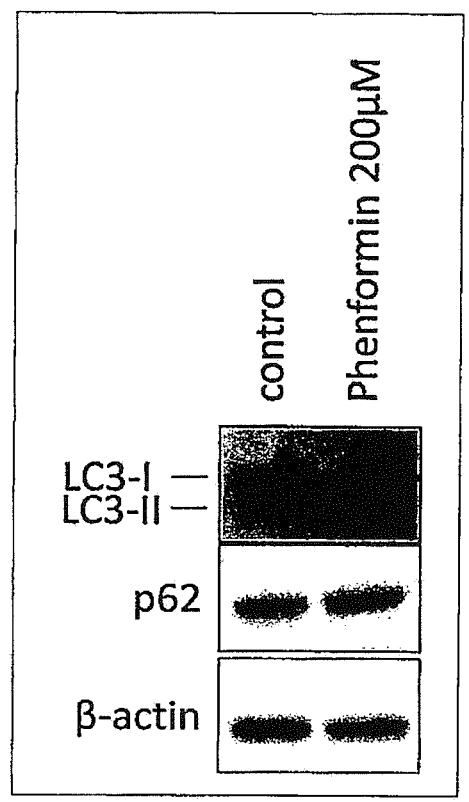

[Figure 12]
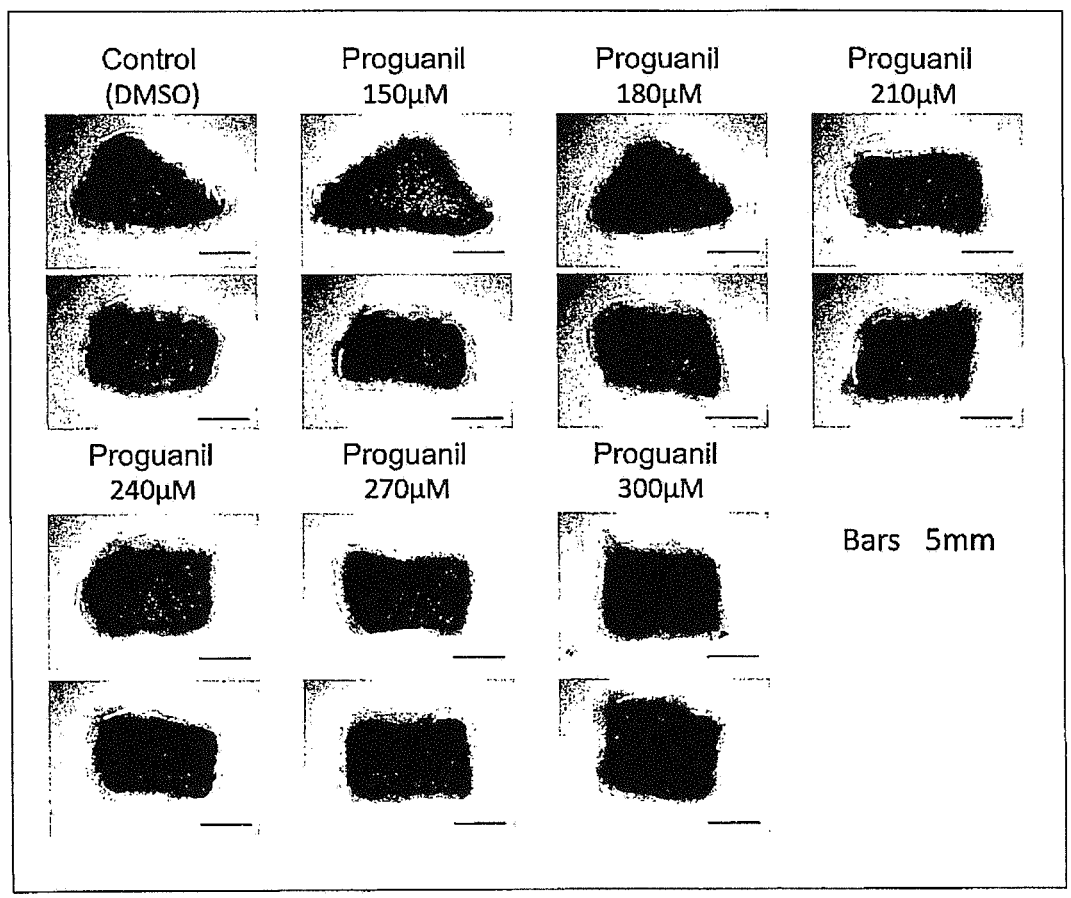

[Figure 13]
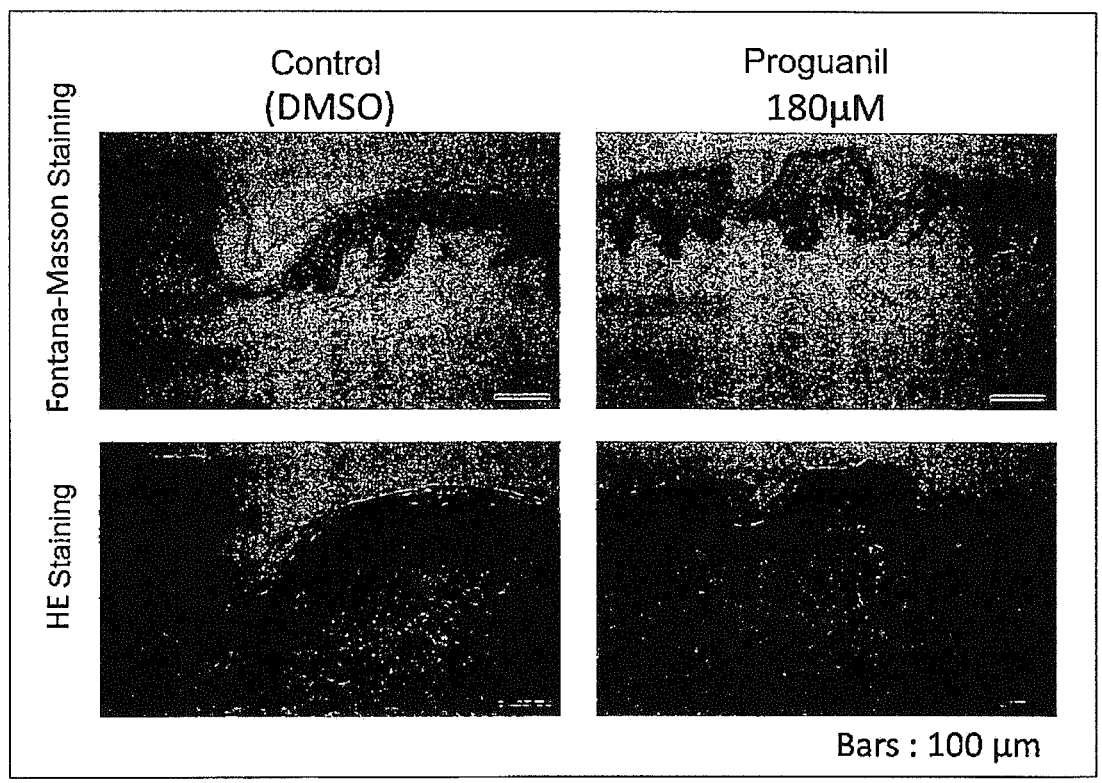

[Figure 14]
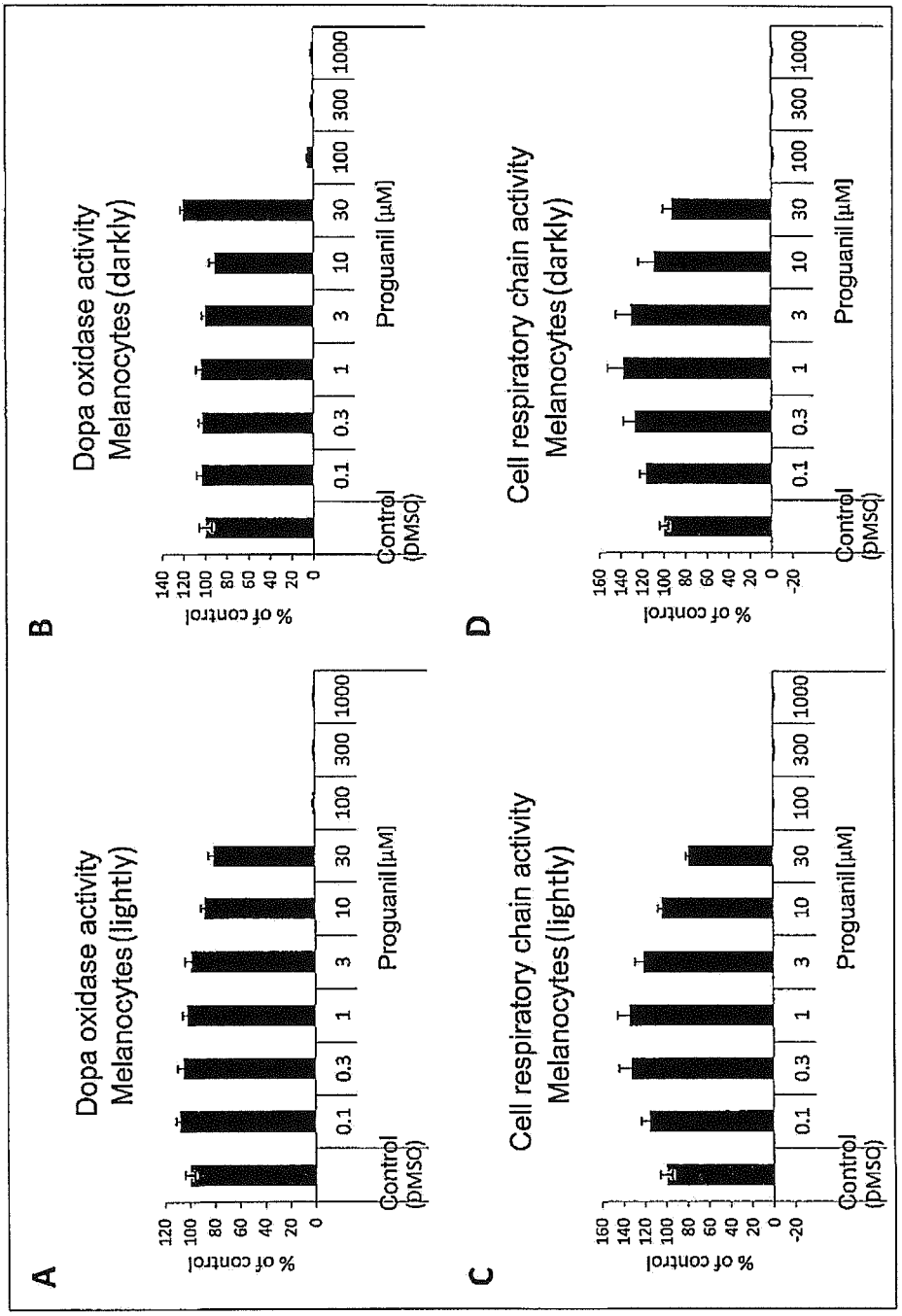

[Figure 15]
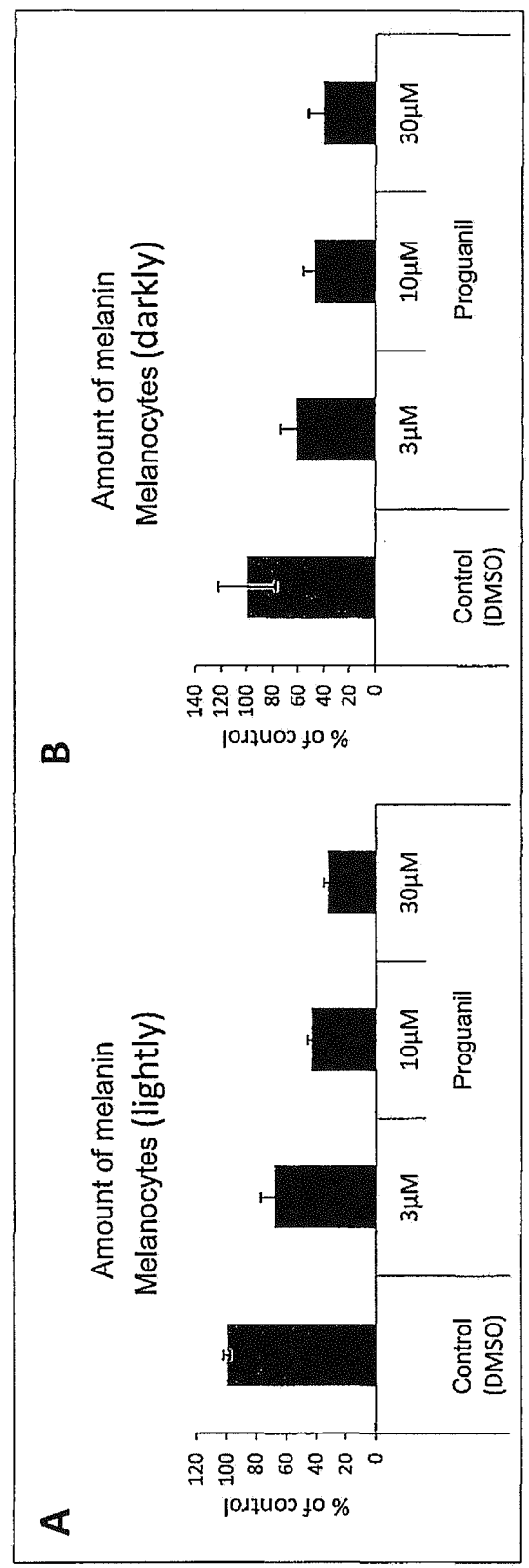

[Figure 16]
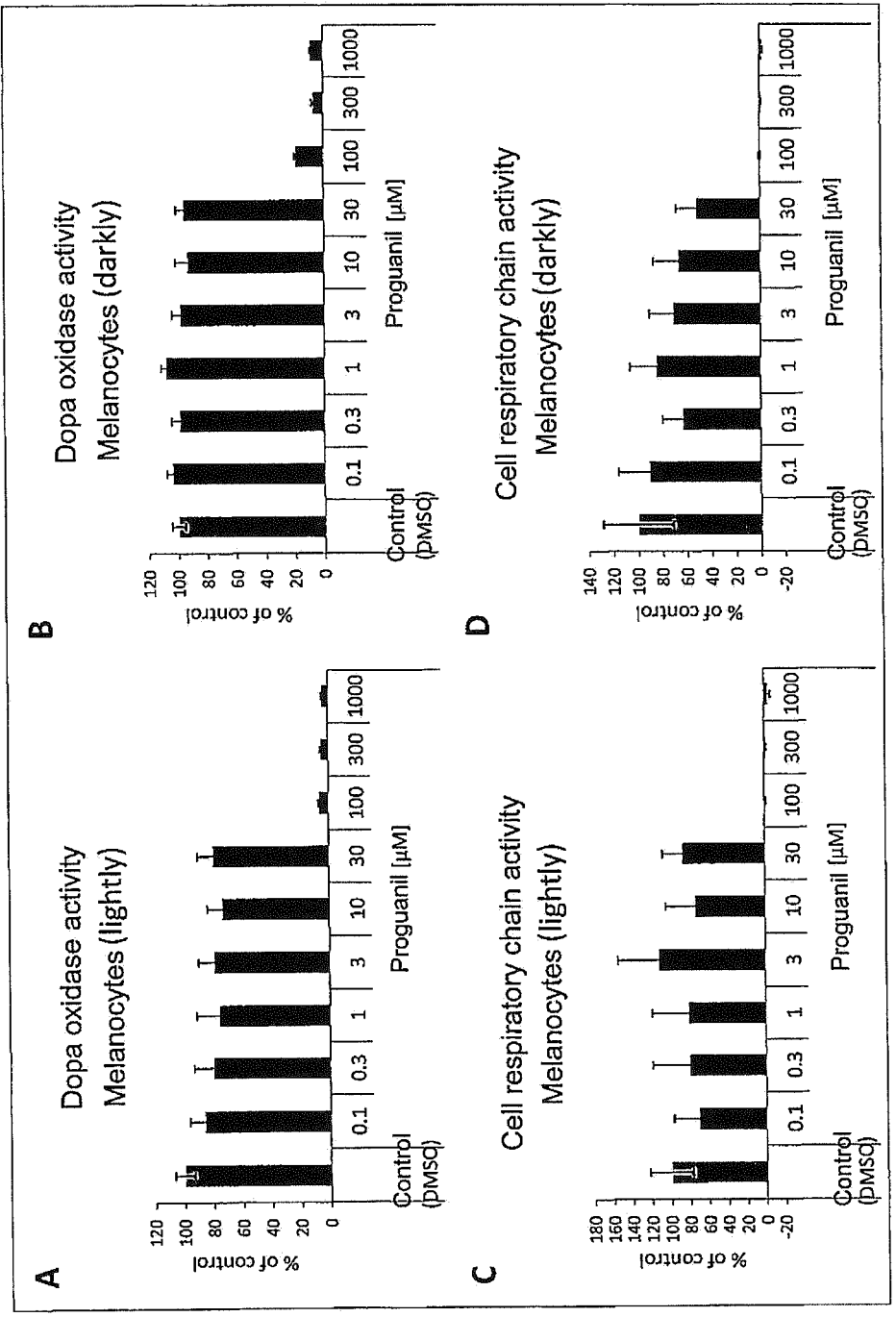

[Figure 17]
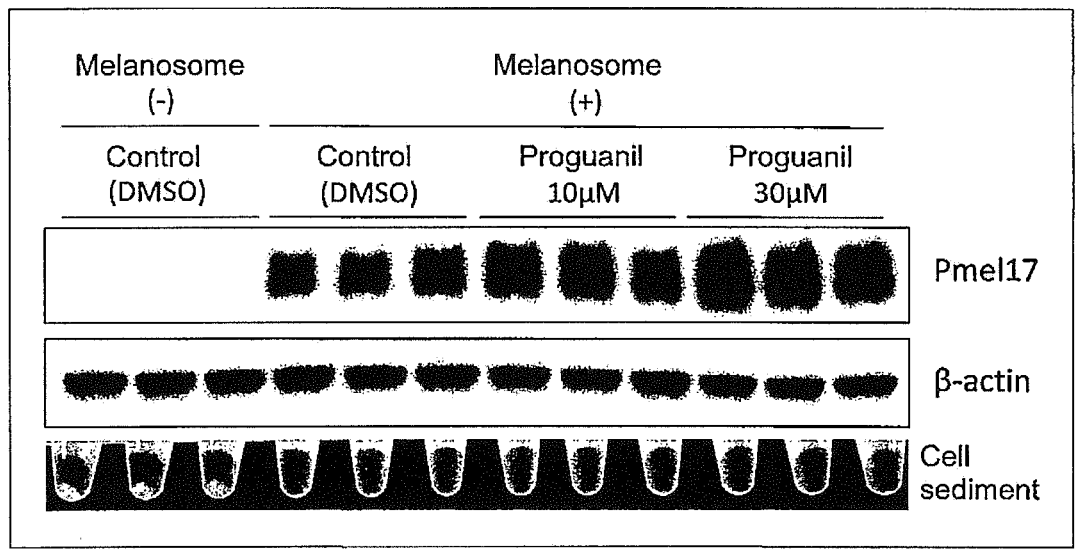
[Figure 18]
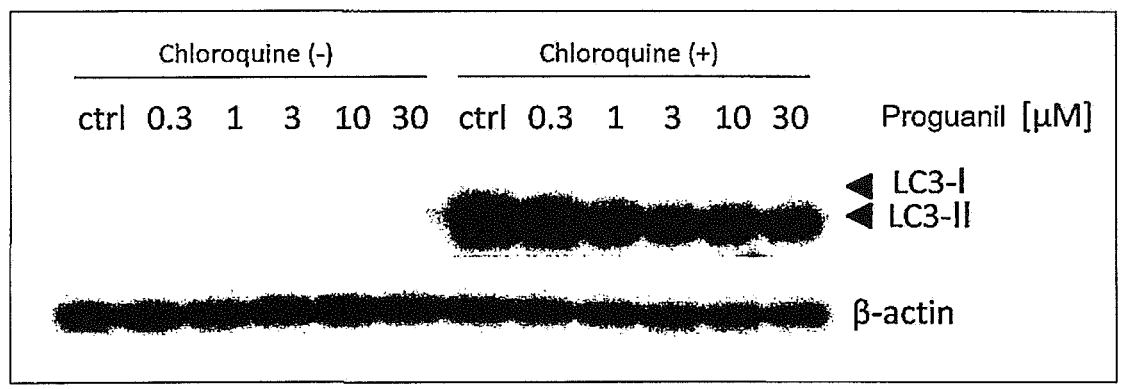

US 10,966,911 B2

MELANIN DECOMPOSITION INHIBITOR

FIELD OF THE INVENTION

The present invention relates to an inhibitor of melanin decomposition which inhibits decomposition of melanin in keratinocytes.

BACKGROUND OF THE INVENTION

It has been reported that various factors are involved in determining color of the skin or hair. Of the various factors, the amount and quality of melanin present in the epidermis are considered to greatly contribute to determining color of the skin or hair. More specifically, generation of color of the skin or hair is significantly influenced by spreading of melanin, which is produced in small organelles called melanosomes in melanin-producing cells (melanocytes), transferred to keratinocytes of the epidermis and hair follicles and distributed over the whole epidermis and hair.

Accordingly, if the amount of melanin is increased in keratinocytes by, e.g., acceleration of melanin production and inhibition of melanin decomposition, the skin turns brown and the hair turns black.

Recently, the applicant found that autophagy is involved in melanin dynamic in keratinocytes and the amount of melanin in keratinocytes is correlated with autophagy activity (Patent Literature 1). According to the finding, if the autophagy activity is inhibited, decomposition of melanin in keratinocytes is inhibited, with the result that the color of the skin or hair can be conceivably darkened.

For the skin, as one of the causes of pigment spots and freckles, acceleration of the activity of melanocytes present in the skin by, e.g., stimulation due to UV-exposure of the skin, abnormality in hormone or genetic factors, to increase melanin production is known. Because of this, whitening agents have been developed for inhibiting melanin production or degrading melanin once produced. However, the number of persons who wish to have brown skin is not small in the United States and European countries. Also, in our country, sunbathing and indoor UV irradiation have been recently in fashion mainly among the youth. In the United States and European countries, artificial tanning on a tanning bed is still popular. In contrast, harmful effects of UV have been acknowledged through enlightenment activities. Owing to this, self-tanning agents containing dihydroxyacetone as a main component are presently available on the market.

Excessive UV irradiation as mentioned above causes significant damage to the skin and may lead to the onset of skin cancer. As to a self-tanning agent, problems in effect have been pointed out. Since a self-tanning agent darkens the skin based on the Maillard reaction of the horny layer, color shade, stability of color shade and UV protection ability are not expected to be improved.

In contrast, getting gray hair is a physiological phenomenon, i.e., aging in which melanin is decreased by a change of hair-matrix melanin-producing cells; however, the mechanism of how to get gray hair has not yet been elucidated. As means for changing gray hair to black hair, a number of components preventing or improving gray hair have been reported; however, sufficient components in view of effectiveness and safety have not yet been obtained. Coloring hair with a hair dye is mainly used at present.

In the circumstances, if a component which directly acts on keratinocytes and increases the amount of melanin or accumulates melanin is found, the component can accelerate a biophylactic ability that melanin inherently has to prevent skin damage as well as darken the skin and prevent or improve gray hair.

Phenformin belongs to the biguanide drug developed as an oral antidiabetic drug. It is reported that phenformin activates autophagy through activation of AMPK (AMP-activated protein kinase) in human embryonic liver cells (HEK 293 T cells) (Non-Patent Literature 1).

Berberine is a benzylisoquinoline alkaloid contained in plants such as KIHADA and OUREN. Since berberine has, e.g., a bactericidal action against harmful enterobacteria and choleretic effect, it is used for treating, e.g., diarrhea. It was reported that berberine has an AMPK activation action (Non-Patent Literature 2); that berberine has an antioxidation and anti-inflammatory effect; and that Barberry root rich in berberine is used as a herb mixture for treating white spot (Non-Patent Literature 3).

Proguanil is an antimalarial agent for use in treating and preventing malaria and a highly safe drug used for a long time over the world.

However, it is totally unknown that phenformin, berberine and proguanil have an inhibitory action on melanin decomposition in keratinocytes.

[Patent Literature 1] International publication 2013/162012

[Non Patent Literature 1] Egan D F, et al., (2011) Science, 331: 456-461

[Non Patent Literature 2] Jeong H W, et al., (2009) Am J Physiol Endocrinol Metab, 296: E955-964

[Non Patent Literature 3] Jimi Yoon, Young-Woo Sun and Tae-Heung Kim (2011). Complementary and Alternative medicine for Vitiligo, Vitiligo-Management and Therapy, Dr. Kelly KyungHwa Park (Ed.), ISBN: 978-953-307-731-4, InTech, Available from: http://www.intechopen.com/books/vitiligo-management-and-therapy/complementary-andalternative-medicine-for-vitiligo

SUMMARY OF THE INVENTION

Detailed Description of the Invention

The present invention relates to the following 1) to 5).

1) An inhibitor of melanin decomposition in keratinocytes, comprising at least one selected from the group consisting of a plant extract containing berberine or a salt thereof, berberine or a salt thereof, proguanil or a salt thereof and phenformin or a salt thereof, as an active ingredient.

2) An inhibitor of autophagy in keratinocytes, comprising at least one selected from the group consisting of a plant extract containing berberine or a salt thereof, berberine or a salt thereof, proguanil or a salt thereof and phenformin or a salt thereof, as an active ingredient.

3) An agent for darkening skin or hair color, comprising at least one selected from the group consisting of a plant extract containing berberine or a salt thereof, berberine or a salt thereof, proguanil or a salt thereof and phenformin or a salt thereof, as an active ingredient.

4) An agent for preventing or improving gray hair, comprising at least one selected from the group consisting of a plant extract containing berberine or a salt thereof, berberine or a salt thereof, proguanil or a salt thereof and phenformin or a salt thereof, as an active ingredient.

5) An external preparation for skin, comprising proguanil or a salt thereof.

BRIEF DESCRIPTION OF DRAWINGS

FIG. 1 Skin color darkening action of phenformin. A: Hispanic, B: African American, C: African American.

FIG. 2 Melanin accumulation action of phenformin. A: Hispanic, B: African American.

FIG. 3 A: Pmel17 protein amount increasing action of phenformin. B: LC3-II and p62 protein amount increasing action of phenformin.

FIG. 4 Skin color darkening action (dose dependent) of phenformin.

FIG. 5 Skin color darkening action and melanin accumulation action of berberine (Caucasian).

FIG. 6 Skin color darkening action and melanin accumulation action of berberine (African American).

FIG. 7 Inhibitory action on autophagy of berberine (epidermal cell).

FIG. 8 Melanosome-decomposition inhibitory action of phenformin, berberine and Goldenseal FIG. 9 Skin color darkening action of OUBAKU extract and OUREN extract.

FIG. 10 Hair color darkening action of phenformin.

FIG. 11 Inhibitory action on autophagy of phenformin.

FIG. 12 Dose-dependent skin color darkening action of proguanil

FIG. 13 Accumulation epidermal melanin deposition of proguanil.

FIG. 14 Effects of proguanil on dopa oxidase activity and cellular respiratory chain activity of melanocytes in a melanocyte single culture system ((A), (C) melanocytes (lightly), (B), (D) melanocytes (darkly)).

FIG. 15 Effects of proguanil on intracellular melanin amount in a melanocyte single culture system ((A) melanocytes (lightly), (B) melanocytes (darkly)).

FIG. 16 Effects of proguanil on dopa oxidase activity and cellular respiratory chain activity of melanocytes in a keratinocyte-melanocyte co-culture system ((A), (C) melanocytes (lightly), (B), (D) melanocytes (darkly)).

FIG. 17 Effect of proguanil on melanin decomposition activity of keratinocytes.

FIG. 18 Effect of proguanil on autophagy activity of keratinocytes.

DETAILED DESCRIPTION OF THE INVENTION

The present invention relates to providing an inhibitor of melanin decomposition, which inhibits decomposition of melanin in keratinocytes and accelerates melanin accumulation in the skin or hair.

The present inventors searched for a substance increasing the amount of melanin in the skin or hair. As a result, they found that phenformin, berberine and proguanil have an inhibitory action on autophagy activity and an inhibitory action on melanin decomposition in keratinocytes and accelerate melanin accumulation in keratinocytes.

According to the present invention, accumulation of melanin in the skin or hair can be accelerated to darken the skin and prevent and improve gray hair.

In the present invention, phenformin and berberine are represented by the following formulas.

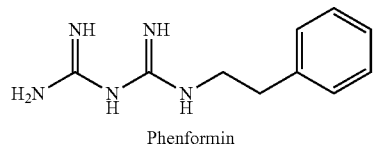
Phenformin

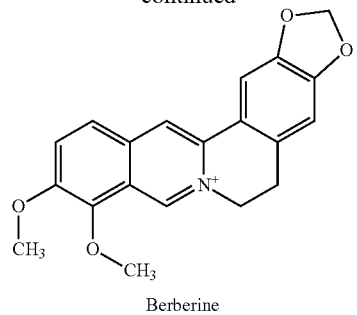
Berberine

In the present invention, a salt of phenformin is not limited as long as it is a pharmaceutically acceptable salt. Examples thereof include salts of inorganic acids (e.g., hydrochloric acid, hydrobromic acid, hydroiodic acid, nitric acid, sulfuric acid, phosphoric acid) and organic acids (e.g., acetic acid, fumaric acid, maleic acid, succinic acid, citric acid, tartaric acid). Preferably, a hydrochloride is used. Phenformin may be used in the form of a hydrate or a solvate.

Phenformin or a salt thereof is available from general reagent manufacturers such as Sigma-Aldrich.

Examples of a salt of berberine include salts of, e.g., hydrochloric acid, sulfuric acid and tannic acid. Preferably a hydrochloride (berberine chloride) is used.

Berberine or a salt thereof is abundantly contained not only in KIHADA and OUREN used as a natural medicine but also in Goldenseal, Barberry and Oregon grape. Highly purified berberine or a salt thereof can be easily obtained by extracting it from these plants and purifying it (13th-edition Japanese Pharmacopoeia, manual, page C-405).

Accordingly, in the present invention, an extract of a plant containing berberine or a salt thereof may be used as berberine or a salt thereof. Examples of the plant containing berberine or a salt thereof include a rutaceous plant, KIHADA (scientific name: *Phellodendron amurense*, medicinal name of bark: OUBAKU), a ranunculaceae plant, OUREN (scientific name: *Coptis japonica*), a ranunculaceae plant, Goldenseal (scientific name: *Hydrastis canadensis*), a Berberidaceae plant, Barberry (scientific name: *Berberis vulgaris*) and a Berberidaceae plant, Oregon grape (scientific name: *Berberis aquifolium*).

Examples of the part of a plant to be used for extraction include, but are not particularly limited to, whole grass, leave, stem, sprout, flower, bud, woody part, bark, thallus, root, rhizome, pseudobulb, bulb, tuber, seed, and fruit. These may be used in combination. Of them, bark is preferably used in the case of KIHADA; and root or rhizome is preferably used in the cases of OUREN, Goldenseal, Barberry and Oregon grape.

A method for producing a plant extract containing berberine or a salt thereof to be used in the present invention is not particularly limited. A plant extract containing berberine or a salt thereof can be obtained from a plant containing berberine or a salt thereof by an extraction method known in the art. In the present invention, an extract produced by a solvent extraction method with a various extraction solvents can be preferably used.

As an extraction solvent, both a polar solvent, and a nonpolar solvent can be used; however, a polar solvent is preferably used in view of extraction efficiency of berberine or a salt thereof. Examples of the polar solvent include water, monovalent to trivalent alcohols such as methanol, ethanol, 1-propanol, 2-propanol, 1-butanol, 2-butanol, tert-butanol, 1-pentanol, 1-hexanol, 1-heptanol, 1-octanol, ethylene glycol, propylene glycol, 1,3-butylene glycol, 1,4-butylene glycol and glycerin, and polyethylene glycol. These solvents may be used alone or in combination of two types or more. In the present invention, in view of physical properties (extraction efficiency, stability), safety and versatility, water, a monovalent to trivalent alcohol or an aqueous solution of a monovalent to trivalent alcohol is preferably used. As the monovalent to trivalent alcohol, ethanol, methanol, 1,3-butylene glycol or glycerin is preferably used.

The amount of an extraction solvent used is not particularly limited as long as a sufficient extraction efficiency is obtained. The amount used can be, for example, from 1 to 1000 mL, preferably from 5 to 100 mL per dry weight (1 g) of a plant.

The extraction condition is not particularly limited as long as sufficient extraction efficiency is obtained. The extraction period (time) can be, for example, one hour or more, preferably one day or more; and 30 days or less, preferably 14 days or less. The extraction is preferably carried out at a temperature of 0° C. or more and equal to or lower than the boiling point of the solvent, more preferably within the range ranging from normal temperature to the boiling point of the solvent. Note that, if the extraction is carried out under pressurized conditions, the extraction temperature is not limited by the boiling point of the solvent to be used and can be appropriately set at an optimal temperature in view of extraction efficiency.

The plant extract as mentioned above may be a crudely purified product as long as it can comply with, for example, cosmetically or pharmaceutically acceptable standards and exerts the effect of the present invention. If necessary, removal of inactive contaminants, deodorization and decoloration may be applied by a technique known in the art, such as liquid-liquid partition, solid-liquid partition, treatment with activated carbon and treatment with ion exchange resin.

The extract as mentioned above can be used as it is or diluted, concentrated or lyophilized to prepare a powder or paste and then put in use. Alternatively, the extract can be lyophilized and dissolved/diluted with a solvent usually used for extraction such as water, ethanol, propylene glycol, a water-ethanol mixed solution, a water-propylene glycol mixed solution, a water-1,3-butylene glycol mixed solution when used, and then put in use. Alternatively, the extract can be enclosed in a vesicle such as liposomes and microcapsules and then put in use.

In the present invention, proguanil refers to 1-(p-chlorophenyl)-5-isopropyl biguanide represented by the following formula.

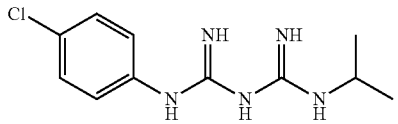 [SMILES: CC(C)NC(=N)NC(=N)Nc1ccc(Cl)cc1]

In the present invention, a salt of proguanil may be a pharmaceutically acceptable salt. Examples thereof include salts of inorganic acids (e.g., hydrochloric acid, hydrobromic acid, hydroiodic acid, nitric acid, sulfuric acid, phosphoric acid) and organic acids (e.g., acetic acid, fumaric acid, maleic acid, succinic acid, citric acid, tartaric acid).

Preferably, a hydrochloride is used. A hydrate or a solvate of proguanil is included in the proguanil of the present invention.

Proguanil or a salt thereof is commercially available; for example, proguanil hydrochloride is commercially offered by, e.g., Sigma-Aldrich.

As shown in Examples (described later), phenformin or a salt thereof, berberine or a salt thereof, a plant extract containing berberine or a salt thereof and proguanil or a salt thereof (referred to as "the compound of the present invention") have an action to increase the amount of Pmel17 protein (Murase D, Hachiya A, Takano K, Hicks R, Visscher M O, Kitahara T, Hase T, Takema Y, Yoshimori T (2013), Autophagy has a significant role in determining skin color by regulating melanosome degradation in keratinocytes, J Invest Dermatol 133: 2416-2424) serving as an index for a melanosome amount in human keratinocytes, accelerate accumulation of melanin and darken the skin color.

Phenformin or a salt thereof, berberine or a salt thereof and a plant extract containing berberine or a salt thereof accelerate accumulation of LC3-II and p62 proteins. LC3-II and p62 proteins are proteins essential for autophagy and generated or decomposed by autophagy and thus used as a marker for autophagy activity (Mizushima N, Yoshimori T (2007), How to interpret LC3 immunoblotting, Autophagy 3: 542-545). Accordingly, the compound of the present invention accelerating accumulation of the above two proteins is considered to have an inhibitory action on autophagy.

Proguanil or a salt thereof also inhibits accumulation of LC3-II in the presence of chloroquine diphosphate, which inhibits proteolysis in autolysosomes. From this, proguanil or a salt thereof is considered to have an inhibitory action on autophagy. Note that, in this case, LC3-II itself is decomposed by autophagy, accurately to say, accumulation of LC3-II during inhibition of decomposition by a decomposition inhibitor serves as a marker for autophagy activity (Mizushima N, Yoshimori T (2007), How to interpret LC3 immunoblotting, Autophagy 3: 542-545).

It has been elucidated that autophagy is involved in decomposition of melanin in keratinocytes (Patent Literature 1). From this, it is considered that accumulation of melanin and increase in the amount of melanin in keratinocytes by the compound of the present invention and resultant skin color darkening are basically caused by inhibition of autophagy activity and inhibition of melanin decomposition in keratinocytes.

Accordingly, if the compound of the present invention is administered to an animal, preferably a human, it is possible to inhibit decomposition of melanin in keratinocytes, inhibit autophagy, darken skin or hair color and prevent or improve gray hair.

More specifically, the compound of the present invention serves as an inhibitor of melanin decomposition in keratinocytes, an inhibitor of autophagy in keratinocytes, an agent for darkening skin or hair color and an agent for preventing or improving gray hair; and can be used for inhibiting melanin decomposition, inhibiting autophagy in keratinocytes, darkening skin or hair color and preventing or improving gray hair.

The phrase "inhibiting autophagy in keratinocytes" herein means inhibiting autophagy activity in keratinocytes, particularly inhibiting generation of phagophores in the autophagy pathway and inhibiting activity to elongate or grow phagophores, thereby increasing the amount of melanin in the keratinocytes.

Note that, autophagy activity can be determined and evaluated not only based on the amount of LC3-II and p62 proteins accumulated but also flux assay in which turnover of these proteins is determined in the presence or absence of a lysosome inhibitor.

The phrase "darkening skin or hair color" means that the color of the skin or hair is darkened by increasing the amount of melanin in the skin or hair having melanin productivity. Accordingly, recovery of the color of skin which lost productivity of melanin, for example, such as the case of vitiligo vulgaris, is not included.

In other words, the inhibitor of melanin decomposition in keratinocytes, inhibitor of autophagy in keratinocytes and agent for darkening skin or hair color according to the present invention do not serve as a therapeutic agent for vitiligo vulgaris; however, if each of them is combined with a therapeutic agent for vitiligo vulgaris, they can be used for inhibiting melanin decomposition and darkening skin color. The present invention does not restrict such use.

In the specification, application of the compound of the present invention to a human may be therapeutic use or non-therapeutic use including cosmetic use.

The "non-therapeutic" use does not include a medical treatment (practice); namely, does not include a surgery, therapy or diagnosis method for a human, more specifically, a concept which does not include a surgery, therapy or diagnosis method practiced on a human by a doctor, a health care worker or a person under a doctor's supervision. Examples of the non-therapeutic use of the compound of the present invention include use for darkening skin or hair color for cosmetic or aesthetic purpose, more specifically, use by, e.g., aestheticians and hairdressers.

In the specification, "improvement" refers to favorable turn of a symptom or a state, preventing or delaying worsening of a symptom or a state, or reversing, preventing or delaying progression of a symptom or a state.

In the specification, "prevention" refers to preventing or delaying occurrence of a symptom in individuals or reducing a risk of occurrence of a symptom in individuals.

The compound of the present invention can be used for producing an inhibitor of melanin decomposition in keratinocytes, an inhibitor of autophagy in keratinocytes, an agent for darkening skin or hair color or an agent for preventing or improving gray hair.

The inhibitor of melanin decomposition in keratinocytes, the inhibitor of autophagy in keratinocytes, the agent for darkening skin or hair color or the agent for preventing or improving gray hair of the present invention can be a medicine, a quasi-drug or a cosmetic for the purpose of inhibiting melanin decomposition, inhibiting autophagy in keratinocytes, darkening of skin or hair color or preventing or improving gray hair, or can be a raw material or a material for producing the medicine, quasi-drug or cosmetic.

The administration route of the medicine or quasi-drug is not limited. Oral administration or parenterally administration may be used. Examples of dosage form for oral administration include solid preparations such as tablet, granule, powder and capsule; and liquid formulations such as elixir, syrup and suspension. Examples of dosage form for parenteral administration include various preparations such as injection, external preparation, transdermal preparation, transmucosal preparation, nasal preparation, enteral preparation, inhalation, suppository and patch. The medicine or quasi-drugs is preferably in the form of an external preparation for skin, more specifically, in the form of ointment, cream, emulsion, lotion, gel, aerosol, patch, tape and spray.

As the form of the cosmetic, any form can be used as long as it is used in cosmetics. Examples thereof include cream, emulsion, lotion, suspension, gel, powder, pack, sheet, patch, stick, cake, hair tonic, hair liquid, hair gel, hair cream, hair treatment, hair spray, aerosol mousse, shampoo and rinse.

Preparation compositions of the medicine, quasi-drug or cosmetic as mentioned above can be individually obtained in accordance with general production methods, more specifically, by blending the compound of the present invention with a pharmaceutically acceptable carrier such as an oil agent, a surfactant, a gelling agent, a preservative, an antioxidant, a solvent, an alcohol, water, a chelating agent, a thickener, a UV absorber, an emulsion stabilizer, a pH modifier, a dye and a perfume, dispersing and processing into a desired form. In each of these preparation compositions, not only the compound of the present invention but also a medicinally effective component such as a plant extract, a germicidal agent, a humectant, an antimicrobial agent and a refreshing agent can be appropriately blended in accordance with the type of preparation such as medicine, quasi-drug and cosmetic, as long as the effect of the present invention is not blocked.

The content of phenformin or a salt thereof, berberine or a salt thereof, a plant extract containing berberine or a salt thereof or proguanil or a salt thereof of the present invention in the preparation composition is generally, in terms of phenformin, berberine or proguanil, preferably 0.01% by mass or more, more preferably 0.05% by mass or more, further preferably 0.1% by mass or more; and preferably 10% by mass or less, more preferably 5% by mass or less, further preferably 2% by mass or less; in other words, preferably from 0.01 to 10% by mass, more preferably from 0.05 to 5% by mass, further preferably from 0.1 to 2% by mass.

The dose of phenformin or a salt thereof, berberine or a salt thereof, a plant extract containing berberine or a salt thereof or proguanil or a salt thereof given by the above preparation composition can be the amount which can achieve the effect of the present invention. The dose can be varied depending on the state, body weight, sex and age of a subject or other factors; however, the dose per adult (60 kg) per day is, in terms of phenformin, berberine or proguanil, for example, preferably 0.1 mg or more, more preferably 1 mg or more, further preferably 5 mg or more; and preferably 5,000 mg or less, more preferably 1,000 mg or less, further preferably 500 mg or less; in other words, preferably from 0.1 to 5,000 mg, more preferably from 1 to 1,000 mg, further preferably from 5 to 500 mg.

In the case where the compound of the invention is administered by applying an external preparation such as a cosmetic, the dose per area of 100 $cm^2$ per time is, in terms of phenformin, berberine or proguanil, preferably 0.01 mg or more, more preferably 0.05 mg or more, further preferably 0.1 mg or more; and preferably 10 mg or less, more preferably 5 mg or less, further preferably 2 mg or less; in other words, preferably from 0.01 to 10 mg, more preferably from 0.05 to 5 mg, further preferably from 0.1 to 2 mg.

The preparation can be ingested or administered in accordance with any dosage regimen. It is preferable that the preparation is administered once or several times per day by dividing the dose into several portions, and continuously administered for several weeks to several months.

As the subject to which the cosmetic, medicine or quasi-drug as mentioned above is to be applied is not particularly limited as long as the subject requires the cosmetic, medicine or quasi-drug, and preferably a human (person) who desires to darken skin and prevent or improve gray hair. Usually, it is preferable to apply the cosmetic, medicine or quasi-drug directly to the site on which the user desires to produce the above effect. As the site on which the user desires to produce the above effect in the case of darkening the skin, a site where the user desires to improve UV protection ability, a site where the user desires to darken the skin for aesthetic purpose are mentioned; more specifically, the skin of face and limbs which are frequently and daily exposed to UV and shown in the public eye, and the skin to which the user applies a self-tanning agent are mentioned. In the case of preventing or improving gray hair, the skin having hair, in particular, the skin of a head having hair is preferable.

In accordance with the embodiment mentioned above, the following aspects are disclosed in the present invention.

<1> An inhibitor of melanin decomposition in keratinocytes, comprising at least one selected from the group consisting of a plant extract containing berberine or a salt thereof, berberine or a salt thereof, proguanil or a salt thereof and phenformin or a salt thereof as an active ingredient.

<2> An inhibitor of autophagy in keratinocytes, comprising at least one selected from the group consisting of a plant extract containing berberine or a salt thereof, berberine or a salt thereof, proguanil or a salt thereof and phenformin or a salt thereof as an active ingredient.

<3> An agent for darkening skin or hair color, comprising at least one selected from the group consisting of a plant extract containing berberine or a salt thereof, berberine or a salt thereof, proguanil or a salt thereof and phenformin or a salt thereof as an active ingredient.

<4> An agent for preventing and improving gray hair, comprising at least one selected from the group consisting of a plant extract containing berberine or a salt thereof, berberine or a salt thereof, proguanil or a salt thereof and phenformin or a salt thereof as an active ingredient.

<5> An external preparation for skin, comprising proguanil or a salt thereof.

<6> In the above item <5>, a content of proguanil or a salt thereof in the external preparation for skin is, in terms of proguanil, preferably 0.01% by mass or more, more preferably 0.05% by mass or more, and further preferably 0.1% by mass or more; and preferably 10% by mass or less, more preferably 5% by mass or less, further preferably 2% by mass or less; in other words, preferably from 0.01 to 10% by mass, more preferably from 0.05 to 5% by mass, further preferably from 0.1 to 2% by mass.

<7> Use of at least one selected from the group consisting of a plant extract containing berberine or a salt thereof, berberine or a salt thereof, proguanil or a salt thereof and phenformia or a salt thereof for producing an inhibitor of melanin decomposition in keratinocytes.

<8> Use of at least one selected from the group consisting of a plant extract containing berberine or a salt thereof, berberine or a salt thereof, proguanil or a salt thereof and phenformin or a salt thereof for producing an inhibitor of autophagy in keratinocytes.

<9> Use of at least one selected from the group consisting of a plant extract containing berberine or a salt thereof, berberine or a salt thereof, proguanil or a salt thereof and phenformin or a salt thereof for producing an agent for darkening skin or hair color.

<10> Use of at least one selected from the group consisting of a plant extract containing berberine or a salt thereof, berberine or a salt thereof, proguanil or a salt thereof and phenformin or a salt thereof for producing an agent for preventing and improving gray hair.

<11> At least one selected from the group consisting of a plant extract containing berberine or a salt thereof, berberine or a salt thereof, proguanil or a salt thereof and phenformin or a salt thereof for use in inhibition of melanin decomposition in keratinocytes.

<12> At least one selected from the group consisting of a plant extract containing berberine or a salt thereof, berberine or a salt thereof, proguanil or a salt thereof and phenformin or a salt thereof for use in inhibition of autophagy in keratinocytes.

<13> At least one selected from the group consisting of a plant extract containing berberine or a salt thereof, berberine or a salt thereof, proguanil or a salt thereof and phenformin or a salt thereof for use in darkening skin or hair color.

<14> At least one selected from the group consisting of a plant extract containing berberine or a salt thereof, berberine or a salt thereof, proguanil or a salt thereof and phenformin or a salt thereof for use in prevention or improvement of gray hair.

<15> In the above items <11> to <14>, a use concentration of the at least one selected from the group consisting of a plant extract containing berberine or a salt thereof, berberine or a salt thereof, proguanil or a salt thereof and phenformin or a salt thereof is, in terms of phenformin, berberine or proguanil, preferably 0.01% by mass or more, more preferably 0.05% by mass or more, further preferably 0.1% by mass or more; and preferably 10% by mass or less, more preferably 5% by mass or less, further preferably 2% by mass or less; in other words preferably from 0.01 to 10% by mass, more preferably from 0.05 to 5% by mass, further preferably from 0.1 to 2% by mass.

<16> Use of at least one selected from the group consisting of a plant extract containing berberine or a salt thereof, berberine or a salt thereof, proguanil or a salt thereof and phenformin or a salt thereof for inhibiting melanin decomposition in keratinocytes.

<17> Use of at least one selected from the group consisting of a plant extract containing berberine or a salt thereof, berberine or a salt thereof, proguanil or a salt thereof and phenformin or a salt thereof for inhibiting autophagy in keratinocytes.

<18> Use of at least one selected from the group consisting of a plant extract containing berberine or a salt thereof, berberine or a salt thereof, proguanil or a salt thereof and phenformin or a salt thereof for darkening skin or hair color.

<19> Use of at least one selected from the group consisting of a plant extract containing berberine or a salt thereof, berberine or a salt thereof, proguanil or a salt thereof and phenformin or a salt thereof for preventing or improving gray hair.

<20> In the above items <16> to <19>, a use concentration of the at least one selected from the group consisting of a plant extract containing berberine or a salt thereof, berberine or a salt thereof, proguanil or a salt thereof and phenformin or a salt thereof is, in terms of phenformin, berberine or proguanil, preferably 0.01% by mass or more, more preferably 0.05% by mass or more, further preferably 0.1% by mass or more; and preferably 10% by mass or less, more preferably 5% by mass or less, further preferably 2% by mass or less; in other words, preferably from 0.01 to 10% by mass, more preferably from 0.05 to 5% by mass, further preferably from 0.1 to 2% by mass.

<21> In the above items <16> to <20>, the above use is preferably non-therapeutic use for darkening skin or hair color or for preventing or improving gray hair for cosmetic or aesthetic purpose.

<22> A method for inhibiting melanin decomposition in keratinocytes, comprising administrating to or ingesting in a subject in need thereof, at least one selected from the group consisting of a plant extract containing berberine or a salt thereof, berberine or a salt thereof, proguanil or a salt thereof and phenformin or a salt thereof in an effective amount.

<23> A method for inhibiting autophagy in keratinocytes, comprising administrating to or ingesting in a subject in need thereof, at least one selected from the group consisting of a plant extract containing berberine or a salt thereof, berberine or a salt thereof, proguanil or a salt thereof and phenformin or a salt thereof in an effective amount.

<24> A method for darkening skin or hair color, comprising administrating to or ingesting in a subject in need thereof, at least one selected from the group consisting of a plant extract containing berberine or a salt thereof, berberine or a salt thereof, proguanil or a salt thereof and phenformin or a salt thereof in an effective amount.

<25> A method for preventing or improving gray hair, comprising administrating to or ingesting in a subject in need thereof, at least one selected from the group consisting of a plant extract containing berberine or a salt thereof, berberine or a salt thereof, proguanil or a salt thereof and phenformin or a salt thereof in an effective amount.

<26> In the above items <22> to <25>, an administration or ingestion amount of the at least one selected from the group consisting of a plant extract containing berberine or a salt thereof, berberine or a salt thereof, proguanil or a salt thereof and phenformin or a salt thereof per adult (60 kg) per day is, in terms of phenformin, berberine or proguanil, preferably 0.1 mg or more, more preferably 1 mg or more and further preferably 5 mg or more; and preferably 5,000 mg or less, more preferably 1,000 mg or less and further preferably 500 mg or less; in other words, preferably 0.1 to 5,000 mg, more preferably 1 to 1,000 mg and further preferably 5 to 500 mg.

<27> In the above items <22> to <25>, the dose of the at least one selected from the group consisting of a plant extract containing berberine or a salt thereof, berberine or a salt thereof, proguanil or a salt thereof and phenformin or a salt thereof per area of 100 cm² per time when applied as an external preparation is, in terms of phenformin, berberine or proguanil, preferably 0.01 mg or more, more preferably 0.05 mg or more, further preferably 0.1 mg or more; and preferably 10 mg or less, more preferably 5 mg or less, further preferably 2 mg or less; in other words, preferably from 0.01 to 10 mg, more preferably from 0.05 to 5 mg, further preferably from 0.1 to 2 mg.

<28> In the above items <22> to <27>, the above method is preferably a non-therapeutic method for darkening skin or hair color or preventing or improving gray hair for a cosmetic or aesthetic purpose.

<29> In the above items <1> to <4> and <7> to <28>, the plant extract containing berberine or a salt thereof is an extract from Oregon grape, KIHADA, OUREN, Barberry or Goldenseal.

<30> In the above item <29>, the plant extract containing berberine or a salt thereof is an extract from root or rhizome of Oregon grape, bark of KIHADA, root or rhizome of OUREN, root or rhizome of Barberry or root or rhizome of Goldenseal.

<31> In the above items <1> to <4> and <7> to <20>, the plant extract containing berberine or a salt thereof is an extract obtained by extracting with a polar solvent.

<32> In the above item <31>, the polar solvent is one or a combination of two or more solvents selected from the group consisting of water, a monovalent to trivalent alcohol such as methanol, ethanol, 1-propanol, 2-propanol, 1-butanol, 2-butanol, tert-butanol, 1-pentanol, 1-hexanol, 1-heptanol, 1-octanol, ethylene glycol, propylene glycol, 1,3-butylene glycol, 1,4-butylene glycol and glycerin, and polyethylene glycol.

<33> In the above item <31>, the polar solvent is water, a monovalent to trivalent alcohol or an aqueous solution of a monovalent to trivalent alcohol.

<34> In the above item <33>, the monovalent to trivalent alcohol is ethanol, methanol, 1,3-butylene glycol or glycerin.

EXAMPLES

Now, the present invention will be more specifically described based on Examples; however, the present invention is not limited by these.

<Preparation of Evaluation Sample>

Phenformin, which was purchased from Sigma-Aldrich, was dissolved in DMSO and then added in a medium at a predetermined concentration.

Berberine, which was purchased from Santa Cruz Biotechnology, was dissolved in DMSO and then added in a medium at a predetermined concentration.

Goldenseal extract, which was purchased from Making Cosmetics, Inc., was added in a medium at a predetermined concentration. This is an extract obtained by using root of Goldenseal as an extraction site and extracting it with an aqueous glycerin solution, and having a solid content of 20%.

OUBAKU extract (OUBAKU Liquid B), which is an extract from bark of KIHADA and purchased from ICHIMARU PHARCOS Co., Ltd., was added in a medium at a predetermined concentration. This is an extract obtained by extraction with 1,3-butylene glycol and having a solid content of 1.25%.

OUREN extract (OUREN Liquid B), which is an extract from OUREN rhizomes and purchased from ICHIMARU PHARCOS Co., Ltd., was added in a medium at a predetermined concentration. This is an extract obtained by extraction with 1,3-butylene glycol and having a solid content of 0.5%.

Proguanil, i.e., proguanil hydrochloride (hereinafter referred to simply as "proguanil"), which was purchased from Sigma-Aldrich, was dissolved in DMSO and then added in a medium at a predetermined concentration.

Example 1

Skin Darkening Action in Human Skin Tissue (1) A normal human skin tissue obtained at the time of a surgical operation was purchased from a Skin Bank of the United States, National Disease Research Interchange (NDRI). The human skin tissue, from which subcutaneous fat was previously removed, was cut into pieces having a size of about 1 cm×about 1 cm by knife and cultured by using a 6-well plate at 37° C. under a 5% $CO_2$ atmosphere. Advanced-DMEM medium containing 10% (v/v) Fetal Bovine Serum (FBS) (Life Technologies, respectively) was used for culture.

(2) The human skin tissue prepared in accordance with the method described in the above (1) was allowed to stand still in the 6-well plate. Then, phenformin was added in the medium so as to have a final concentration of 300 μM and tissue culture was initiated. The medium replacement was performed every 2 to 3 days. Six days or eight days later, the appearance of the skin tissue was observed and photographed.

Skin tissues derived from a Hispanic person and two African Americans (Hispanic: skin tissue of Day 8 of culture; African American: skin tissue of Day 6 of culture) were evaluated. As a result, in all of the culture experiments, apparent darkening of skin color was induced by phenformin (FIGS. 1A-1C).

(3) Next, the skin tissue cultured was subjected to Fontana-Masson staining to observe deposition of melanin. In the staining, Fontana-Masson Stain Kit manufactured by American Mastertech Scientific, Inc. was used.

In the skin tissues derived from Hispanic (skin tissue of FIG. 1A) and the skin tissues derived from African Americans (skin tissue of FIG. 1B) treated with phenformin, significant accumulation of melanin in the epidermis was observed (FIGS. 2A and 2B). As shown in magnified images, melanin deposition in a wide range of the epidermis from the basal layer to the spinous layer and granular layer was observed when phenformin was added.

Example 2

Melanin Accumulation Acceleration Action in Human Skin Tissue

The skin tissue derived from an African American and prepared in accordance with the method of Example 1 (1) was allowed to stand still in a 6-well plate and cultured in the presence or absence of phenformin for 6 days. Protein was extracted from the skin tissue and used for quantitative analysis of Pmel17 protein, which is a major protein constituting a melanosome, by Western-blotting. Using a mouse anti-human Pmel17 antibody (DAKO) as a primary antibody and a goat anti-mouse IgG antibody as a secondary antibody, signals were detected by using ECL prime reagent (GE Healthcare) and ODYSSEY Fc Imaging System (LICOR). Beta-actin protein as an internal standard was detected in the same manner. It was observed that the amount of Pmel17 protein is increased by phenformin, which is in conformity with induction of melanin deposition (FIG. 3A).

Example 3

Inhibitory Action on Autophagy in Human Skin Tissue

Further, the skin tissue derived from an African American and prepared in accordance with the method of Example 1 (1) was allowed to stand still in a 6-well plate and cultured in the absence or presence of phenformin at a different concentration for 4 days. Proteins were extracted from the skin tissues and subjected to Western-blotting analysis. In this manner, the expression levels of LC3-II and p62 proteins, which are localized in autophagosome membrane and finally decomposed by autophagy, were determined. A mouse anti-human LC3 antibody (Cosmo Bio) and rabbit anti-human p62 antibody (MBL International) were used as primary antibodies. Since accumulation on both markers was observed by addition of phenformin, inhibition autophagy was suggested (FIG. 3B).

Example 4

Skin Color Darkening Action (Dose Dependent) in Human Skin Tissue

A human skin tissue prepared in accordance with the method of Example 1 (1) was allowed to stand still in a 6-well plate. Then, phenformin was added in a medium at a final concentration of 100, 200 or 300 μM and tissue culture was initiated. Four days later, the appearance of the skin tissue was observed and photographed. Recognizable darkening was observed in a dose-dependent manner by 4-day treatment (FIG. 4). Note that, melanin deposition, which is correlated with a change in skin color, was confirmed by Fontana-Masson staining (data not shown).

Skin tissues derived from a Caucasian and an African American and prepared in accordance with the method of Example 1 (1) were allowed to stand still in 6-well plates. Berberine was added to the medium for the skin tissue derived form a Caucasian at a final concentration of 10 or 30 μM and to the medium for the skin tissue derived from an African American at a final concentration of 30 or 100 μM. Then, tissue culture was initiated. Six days later or four days later, the appearance of the skin tissues was observed and photographed.

In all (skin tissue) specimens, darkening of skin color was induced in a berberine dose-dependent manner. Deposition of melanin on the epidermal layer was confirmed also by tissue staining (FIGS. 5 and 6).

Example 5

Inhibitory Action on Autophagy of Berberine

As a part of elucidation of the skin color darkening action of berberine, the effect on autophagy in epidermal cells was examined. Berberine was added in a medium for the epidermal cells seeded in a 6-well plate at a final concentration of 10, 30 or 60 μM and the epidermal cells were cultured for 24 hours. Protein was extracted and subjected to Western-blotting analysis to determine the expression levels of LC3-II and p62 proteins serving as markers for autophagy. It was observed that LC3-II and p62 proteins are accumulated in a berberine dose-dependent manner. From this, inhibitory action on autophagy was suggested (FIG. 7).

Example 6

Melanosome-Decomposition Inhibitory Action

As a part of elucidation of skin color darkening action of phenformin and berberine, an effect of phenformin and berberine on melanosome decomposition in, epidermal cells was examined. The epidermal cells were isolated from a foreskin tissue obtained from a Skin Bank of the United States, National Disease Research Interchange (NDRI) in accordance with a predetermined method, and cultured. Melanosomes were prepared from MNT-1 cell strain in accordance with a predetermined method (Murase et al. (2013), J Invest Dermatol, 133: 2416-2424). A predetermined amount of melanosomes was added to epidermal cells and the cells were cultured for 24 hours. Melanosome prepared from MNT-1 cell strain cultured in an area of 35 cm$^2$ was added per well of the 6-well plate. After the cells were washed with PBS, the epidermal cells which had incorporated melanosome therein were added with phenformin at a final concentration of 100 or 200 μM, berberine at a final concentration of 10, 30 or 60 μM and a Goldenseal extract rich in berberine at a final concentration 0.2 or 0.5% (v/v), and the cells were cultured for a further 24 hours. Protein was extracted and subjected to Western-blotting analysis to determine the expression level of Pmel17, a major protein constituting melanosome. Even when any one of the components was added, accumulation of Pmel17 protein in a dose-dependent manner was observed. From this, melanosome-decomposition inhibitory action was suggested (FIG. 8).

Example 7

Skin Color Darkening Action of OUBAKU Extract and OUREN Extract

The skin tissue derived from an African American and prepared in accordance with the method of Example 1 (1) was allowed to stand still in a 6-well plate. Each of an OUBAKU extract and an OUREN extract were added in a medium at a final concentration of 10 (V/V) and tissue culture was initiated. Six days later, appearance of the skin tissue was observed and photographed.

In all (skin tissue) specimens, darkening of skin color was induced by addition of the OUBAKU extract and the OUREN extract. Melanin deposition in the epidermal layer was also confirmed also by tissue staining (FIG. 9).

Example 8

Hair Color Darkening Action of Phenformin

A human hair follicle was surgically isolated from a normal human scalp tissue (derived from a Caucasian), which was obtained at the time of surgical operation, and given by a USA dermatologist. The isolated human hair follicle was cultured at 37° C. under a 5% $CO_2$ atmosphere in William E medium supplemented with 20 μg/mL insulin (Sigma-Aldrich), 40 ng/mL hydrocortisone (Sigma-Aldrich), 2 mM L-glutamine (Life Technologies) and a 1% (v/v) penicillin/streptomycin solution (Life Technologies) (all were final concentrations). The isolated human hair follicle was allowed to stand still in a 24-well plate and phenformin was added at a final concentration of 200 μM in the medium. Tissue culture was initiated. Medium replacement was performed Day 1 and Day 3 after the initiation of culture. Follicular tissue at Day 5 after the initiation of culture was embedded in OCT compound (TissueTek) and frozen. These follicular tissues were subjected to Fontana-Masson staining and deposition of melanin was observed. Apparent hair color darkening was induced by a treatment of phenformin in the follicular tissue cultured (FIG. 10).

Example 9

Inhibitory Action on Autophagy of Phenformin in Human Hair Follicle

From the human hair follicle cultured in accordance with the method of Example 8, protein was extracted and subjected to Western-blotting analysis. In this manner, expression levels of autophagy markers, i.e., LC3-II and p62 proteins, were analyzed. Accumulation of LC3-II and p62 proteins by addition of phenformin was observed. From this, inhibitory action on autophagy was suggested (FIG. 11).

Example 10

Effect of Proguanil on Skin Color (1) Tissue Culture

A normal human skin tissue, which was obtained at the time of surgical operation, was provided by a medical college (department of plastic surgery).

The human skin tissue, from which subcutaneous fat was previously trimmed, was cut into small pieces having a size of about 1 cm×1 cm by knife. The small pieces were cultured by using a 6-well plate at 37° C. under a 5 vol % $CO_2$ atmospheric conditions. In the culture, Advanced DMEM medium containing a 10% (v/v) Fetal Bovine Serum (FBS) (Thermo Fisher Scientific, respectively) was used.

(2) Effect of Proguanil on Skin Color

A human skin tissue was allowed to stand still in a 6-well plate. Proguanil was added in the medium at a final concentration of 150, 180, 210, 240, 270 or 300 μM and then tissue culture was performed. As a control, DMSO was added in the same amount. Medium replacement was carried out every 2 to 3 days. Day 5 after initiation of the culture, the appearance of the skin tissue was observed and photographed. As a result, it was confirmed that proguanil induces darkening of the skin color in a dose-dependent manner (FIG. 12).

(3) Staining of Tissue Section and Observation Thereof

The skin tissue cultured in the medium added with proguanil at a final concentration of 180 μM for 5 days, in which darkening of skin color had been induced to the extent that the researcher was able to visually observe, was subjected to Fontana-Masson staining to observe deposition of melanin. More specifically, the skin tissue was embedded in paraffin and the resultant paraffin block was sliced to prepare paraffin sections of 5 μm in thickness. A Fontana ammonia silver solution (manufactured by MUTO PURE CHEMICALS Co., Ltd.) was allowed to react at room temperature for two hours to visually distinguish melanin granules. Thereafter, nuclear staining was performed using Kernechtrot solution (manufactured by MUTO PURE CHEMICALS Co., Ltd.). It was observed that melanin is accumulated in a wider range of the epidermis in the skin obtained by adding proguanil (180 μM), as compared to the skin (control) obtained by adding DMSO (FIG. 13; upper stage). At the same time, HE staining was carried out. As a result, it was confirmed that no damage was induced in the tissue by adding proguanil (FIG. 13; lower stage).

Example 11

Effect of Proguanil on Melanin Production in Melanocyte Single Culture System (1) Cell Culture Normal human neonatal foreskin-derived epidermal melanocytes (Human Epidermal Melanocytes, neonatal, lightly pigmented donor (HEMn-LP) and Human Epidermal Melanocytes, neonatal, darkly pigmented donor (HEMn-DP); melanocytes (lightly) and melanocytes (darkly)), a growth medium for epidermal melanocytes (Medium254) and a growth additive (HMGS) for the medium were purchased from Thermo Fisher Scientific. Melanocytes were cultured at 37° C. in 5 vol % $CO_2$ atmospheric conditions.

(2) Effect of Proguanil on Dopa Oxidase Activity of Melanocytes in Melanocyte Single Culture System Melanocytes (lightly and darkly) were seeded in 96-well plates at a cell density of $2 \times 10^4$ cells/well (100 μL/well). As a test medium herein, Medium254 was used, which contained, as growth additives (HMGS), Fetal Bovine Serum (FBS), a basic fibroblast growth factor (hFGF-B; Human Fibroblast growth factor-basic), hydrocortisone, insulin, transferrin, heparin and Bovine Pituitary Extract (BPE) and did not contain phorbol 12-myristate 13-acetate (PMA). Two days later, proguanil was added at a final concentration of 0.1, 0.3, 1, 3, 10, 30, 100, 300 or 1000 μM and culture was performed at 37° C. in 5 vol % $CO_2$ atmospheric conditions for 4 days. As a control, the same amount of DMSO was added. After completion of culture, the whole medium was replaced (100 µL/well), a reagent, alamarBlue (Bio-Rad AbD Serotec Limited) was added so as to obtain a ratio of 10 µL/well. Incubation was carried out at 37° C. in 5 vol % $CO_2$ atmospheric conditions for one hour. Thereafter, fluorescence intensity of the medium was measured ($Ex_{544\ nm}/Em_{590\ nm}$) to evaluate cellular respiratory chain (growth) activity. Thereafter, cell culture plates were washed three times with PBS and an extraction Buffer (0.1M Tris-HCL (pH: 7.2), 1% NP-40, 0.01% SDS) was added in an amount of 20 µL/well, and Assay Buffer (4% dimethylformamide, 100 mM Sodium phosphate-buffered (pH: 7.1)) in an amount of 20 µL/well. The cells were lysed at 4° C. over 2 hours and dopa oxidase activity was measured. The activity measurement was performed by the following method based on the METH method (Winder A. et al., 1991, Eur. J. Biochem. 198: 317-326): to individual wells containing a cell lysate, the Assay Buffer (80 µL) as mentioned above, an aqueous 20.7 mM MBTH (3-methyl-2-benzothiazolinone hydrazone) solution (60 µL) and an aqueous 5 mM L-DOPA (L-dihydroxyphenylalanine) (40 µL) solution serving as a substrate were added, a reaction was performed at 37° C. for 30 minutes and the absorbance at a wavelength of 505 nm was measured.

As a result, proguanil did not accelerate dopa oxidase activity, as compared to the control obtained by adding DMSO alone (FIGS. 14A, 14B). In the concentration range of 30 µM or less, cell toxicity was not observed (FIGS. 14C, 14D).

(3) Effect of Proguanil on Intracellular Melanin Amount of Melanocytes in Melanocyte Single Culture System Melanocytes (lightly and darkly) were seeded in 6-well plates at a cell density of $2 \times 10^5$ cells/well (2 mL/well). As a test medium herein, Medium254 was used, which contained, as growth additives (HMGS), Fetal Bovine Serum (FBS), a basic fibroblast growth factor (hFGF-B; Human Fibroblast growth factor-basic), hydrocortisone, insulin, transferrin, heparin and Bovine Pituitary Extract (BPE) and did not contain phorbol 12-myristate 13-acetate (PMA). The following day, proguanil was added at a final concentration of 3, 10 or 30 µM and culture was performed at 37° C. in 5 vol % $CO_2$ atmospheric conditions for 7 days. As a control, the same amount of DMSO was added. Note that medium replacement was carried out every 2 to 3 days. After completion of culture, the cell culture plates were washed with PBS and the cells were collected by use of a cell scraper in 1.5 mL micro tubes. To individual tubes, 2M NaOH (150 µL) was added and treatment was performed at 100° C. for 60 minutes to lyse the cells. Each of the lysates was centrifuged at a 21,640 g for 10 minutes at room temperature and the supernatant was recovered. The absorbance of the supernatant recovered was measured at a wavelength of 405 nm and the amount of melanin per well was calculated.

As a result, it was found that proguanil does not increase intracellular amount of melanin, as compared to the control obtained by adding DMSO alone (FIGS. 15A, 15B).

Example 12

Effect of Proguanil on Melanin Production in a Coculture System of Keratinocytes and Melanocytes (1) Cell Culture Normal human neonatal foreskin-derived epidermal keratinocytes (Human Epidermal Keratinocytes, neonatal (HEKn) lightly; keratinocytes) and growth medium (Epilife) for epidermal keratinocytes were purchased from Thermo Fisher Scientific. Growth additives (Humedia-KG) for a medium were purchased from Kurabo Industries Ltd. Normal human neonatal foreskin-derived epidermal melanocytes (Human Epidermal Melanocytes, neonatal, lightly pigmented donor (HEMn-LP) and Human Epidermal Melanocytes, neonatal, darkly pigmented donor (HEMn-DP); melanocytes (lightly) and melanocytes (darkly)) were purchased from Thermo Fisher Scientific. Keratinocytes and melanocytes were cultured at 37° C. in 5 vol % $CO_2$ atmospheric conditions.

(2) Effect of Proguanil on Dopa Oxidase Activity of Melanocytes in Co-Culture System Keratinocytes were seeded in a 96-well plate at a cell density of $1 \times 10^4$ cells/well (100 µL/well). On the following day, melanocytes (lightly and darkly) were seeded at a cell density of $2 \times 10^4$ cells/well (100 µL/well). On the following day, proguanil was added at a final concentration of 0.1, 0.3, 1, 3, 10, 30, 100, 300 or 1000 µM. Culture was performed at 37° C. in a 5 vol % $CO_2$ atmospheric conditions for 4 days. As a test medium at this time, Epilife was used, which contained Humedia-KG growth additive (insulin, hydrocortisone, BPE, gentamicin and amphotericin B) except a Human Epidermal Growth Factor (hEGF). As the control, the same amount of DMSO was added. After completion of culture, cellular respiratory chain (growth) activity and dopa oxidase activity were evaluated in the same manner as in Example 11. As a result, it was found that proguanil does not accelerate dopa oxidase activity, as compared to the control obtained by adding DMSO alone (FIGS. 16A, 16B). In the concentration range of 30 µM or less, cell toxicity was not observed (FIGS. 16C, 16D).

Example 13

Effect of Proguanil on Epidermal Keratinocytes (1) Cell Culture

Normal human neonatal foreskin-derived epidermal keratinocytes (Human Epidermal Keratinocytes, neonatal (HEKn) lightly; keratinocytes) were purchased from Thermo Fisher Scientific. Melanoma cell strain MNT-1 cells were given by Dr. Natali (University La Sapienza, Rome, Italy). The keratinocytes were cultured in a grow medium (Epilife) epidermal keratinocytes (Thermo Fisher Scientific) supplemented with a growth additive (Humedia-KG) (manufactured by Kurabo Industries Ltd.) at 37° C. in 5 vol % $CO_2$ atmospheric conditions. As a grow medium MNT-1 cells, RPMI1640 medium (Thermo Fisher Scientific) containing AIM-V medium and Fetal Bovine Serum (FES) each in an amount of 10% (v/v) was used and culture was performed at 37° C. in 5 vol % $CO_2$ atmospheric conditions.

(2) Preparation of Melanosome Fraction

A melanosome fraction was isolated and prepared from MNT-1 cells by a predetermined method (Murase et al. (2013), J Invest Dermatol, 133: 2416-2424). More specifically, MNT-1 cells, which were cultured in a flask (175 cm$^2$) and reached confluent, were recovered with 0.05% Trypsin/EDTA (Thermo Fisher Scientific) and washed with Phosphate-Buffered Saline (DPBS, no calcium, no magnesium; Thermo Fisher Scientific) (hereinafter simply referred to as PBS). Subsequently, 2 mL of Lysis buffer (0.1M Tris-HCL, pH7.5, 1% Igepal CA-630, 0.01% SDS) was added. The mixture was gently mixed and stirred at 4° C. for one hour while shaking. The resultant cell lysate was dispensed in 1.5 mL micro tubes and centrifuged at 1,000 g for 10 minutes (4° C.) and the supernatant was recovered. The centrifugal operation was repeated twice. Subsequently, the supernatant was obtained and centrifuged at 20,000 g for 10 minutes (4° C.). Finally, the pellet was washed with PBS. The centrifugal operation was repeated twice in the same conditions. The pellet obtained was regarded as a melanosome fraction (melanosome-rich fraction).

(3) Effect of Proguanil on Melanin (Melanosome) Decomposition in Epidermal Keratinocytes Keratinocytes were seeded in a 6-well plate at a cell density of $2\times10^5$ cells/well (2 mL/well). Three days later, a melanosome fraction obtained from MNT-1 cells cultured in a flask (175 cm$^2$) was added in 6-wells of the plate so as to equally distribute therein. The following day, medium replacement was performed. Proguanil was added so as to obtain a final concentration of 10 or 30 µM. Culture was performed at 37° C. in 5 vol % $CO_2$ atmospheric conditions for 2 days. As a control, the same amount of DMSO was added. Note that, as the test medium herein, Epilife was used, which contained, as growth additives (Humedia-KG), hydrocortisone, insulin, gentamicin and amphotericin B and did not contain Human Epidermal Growth Factor (hEGF) or Bovine Pituitary Extract (BPE). After completion of culture, cells were washed with PBS, recovered with RIPA buffer (Sigma-Aldrich) and ultrasonically crushed. Thereafter, the crushed cells were centrifuged at 15,000 rpm for 15 minutes. The resultant supernatant was subjected to quantitative determination of protein by BCA (bicinchoninic acid) method using Pierce BCA Protein Assay Kit (Thermo Fisher Scientific) and Bovine Serum Albumin (BSA) as a standard substance. Thereafter, samples were prepared so as to contain the same amount of protein and subjected to SDS-PAGE and Western Blotting in accordance with routine methods. As a primary antibody, anti-Pmel17 (Dako, 1:250) was used. As a secondary antibody, an anti-mouse IgG, HRP-Linked F(ab')$_2$ Fragment Sheep (GE Healthcare Life Science) was used. Thereafter, color was developed by using ECL plus western blotting detection reagents (GE healthcare bioscience) and the expression level was visualized by using LAS4000 (Fuji Film). Expression of β-actin as the internal standard was evaluated by using a monoclonal antibody specific for β-actin (Sigma-Aldrich, 1:5000). The intensity of the band of a Pmel17 detected in keratinocytes having melanosome incorporated therein and treated with proguanil is increased in a concentration-dependent manner, as compared to the control obtained by adding DMSO. The color density of the cell sediment recovered was confirmed to be increased in a concentration-dependent manner (FIG. 17). Since Pmel17 is a protein specific to melanosome, it was considered that decomposition of melanosome incorporated in keratinocytes is inhibited by treatment with proguanil.

(4) Effect of Proguanil on Autophagy Activity of Epidermal Keratinocytes

Keratinocytes were seeded in a 6-well plate at a density of $1.5\times10^5$ cells/well (2 mL/well). The following day, proguanil was added so as to obtain a final concentration of 0.3, 1, 3, 10 or 30 µM. Culture was performed at 37° C. in 5 vol % $CO_2$ atmospheric conditions. As a control, the same amount of DMSO was added. Note that, as the test medium herein, Epilife was used, which contained, as growth additives (Humedia-KG), hydrocortisone, insulin, gentamicin and amphotericin B and did not contain Human Epidermal Growth Factor (hEGF) or Bovine Pituitary Extract (BPE). The following day, Chloroquine diphosphate attached to LC3B Antibody Kit for Autophagy (Thermo Fisher Scientific) was added so as to obtain a final concentration of 10 µM. Culture was performed at 37° C. in 5 vol % $CO_2$ atmospheric conditions for 24 hours. After completion of the culture, SDS-PAGE and western blotting were performed in accordance with the method as mentioned above. As a primary antibody, anti-LC3B (1:1000) attached to the kit mentioned above was used. As a secondary antibody, an anti-rabbit IgG, HRP-Linked F(ab')$_2$ Fragment Sheep (GE Healthcare Life Science) was used. Thereafter, color was developed by using ECL plus western blotting detection reagents (GE healthcare bioscience) and the expression level was visualized by using LAS4000 (Fuji Film). Expression of β-actin as the internal standard was evaluated by using monoclonal antibody specific for β-actin (Sigma-Aldrich, 1:5000). Accumulation of LC3-II was induced by addition of an lysosome inhibitor, Chloroquine diphosphate; however, the accumulation was reduced by proguanil in a concentration-dependent manner (FIG. 18). This conceivably means that proguanil inhibits autophagy activity in a (previous) stage before formation of autophagosome membrane. Accordingly, it is considered that proguanil inhibits melanin decomposition in keratinocytes by inhibiting autophagy activity of the keratinocytes.

What is claimed is:

1. A method for inhibiting melanin decomposition in a subject's keratinocytes, comprising externally applying, to a site on the subject's skin at which the subject desires to inhibit melanin decomposition, an effective amount of an external preparation that comprises proguanil or a salt thereof and inhibiting melanin decomposition at the site as a result of the applying.

2. A method for inhibiting autophagy in a subject's keratinocytes, comprising externally applying, to a site on the subject's skin at which the subject desires to inhibit the autophagy, an effective amount of an external preparation that comprises proguanil or a salt thereof and inhibiting autophagy at the site as a result of the applying.

3. A method for darkening a subject's skin or hair color, comprising externally applying, to a site on the subject's skin or hair at which the subject desires to darken the subject's skin or hair color, an effective amount of an external preparation that comprises proguanil or a salt thereof and darkening the subject's skin or hair color at the site as a result of the applying.

4. A method for improving a subject's gray hair, comprising externally applying to a site on the subject's skin or hair at which the subject desires to improve gray hair, an effective amount of an external preparation that comprises proguanil or a salt thereof and improving the subject's gray hair at the site as a result of the applying.

5. The method according to claim 1, wherein the amount of proguanil that is applied per adult, is 0.1 to 5,000 mg per day.

6. The method according to claim 2, wherein the amount of proguanil that is applied per adult, is 0.1 to 5,000 mg per day.

7. The method according to claim 3, wherein the amount of proguanil that is applied per adult, is 0.1 to 5,000 mg per day.

8. The method according to claim 4, wherein the amount of proguanil that is applied per adult, is 0.1 to 5,000 mg per day.

9. The method according to claim 1, wherein the dose of proguanil per area of 100 cm$^2$ per application is from 0.01 to 10 mg.

10. The method according to claim 2, wherein the dose of proguanil per area of 100 cm$^2$ per application is from 0.01 to 10 mg.

11. The method according to claim 3, wherein the dose of proguanil per area of 100 cm$^2$ per application is from 0.01 to 10 mg.

12. The method according to claim 4, wherein the dose of proguanil per area of 100 cm$^2$ per application is from 0.01 to 10 mg.

* * * * *